US010916332B2

(12) United States Patent
Silver

(10) Patent No.: US 10,916,332 B2
(45) Date of Patent: *Feb. 9, 2021

(54) METHODS AND SYSTEMS FOR GENERATING A VIRTUAL PROGENY GENOME

(71) Applicant: Ancestry.com DNA, LLC, Lehi, UT (US)

(72) Inventor: Lee M. Silver, New York, NY (US)

(73) Assignee: Ancestry.com DNA, LLC, Lehi, UT (US)

( * ) Notice: Subject to any disclaimer, the term of this patent is extended or adjusted under 35 U.S.C. 154(b) by 871 days.

This patent is subject to a terminal disclaimer.

(21) Appl. No.: 14/293,541

(22) Filed: Jun. 2, 2014

(65) Prior Publication Data

US 2015/0088429 A1 Mar. 26, 2015

Related U.S. Application Data

(63) Continuation of application No. 12/908,636, filed on Oct. 20, 2010, now Pat. No. 8,805,620.

(60) Provisional application No. 61/253,108, filed on Oct. 20, 2009.

(51) Int. Cl.
*G16B 20/00* (2019.01)
*G16H 50/30* (2018.01)
*C12Q 1/6827* (2018.01)
*G16B 10/00* (2019.01)

(52) U.S. Cl.
CPC ........... *G16B 20/00* (2019.02); *C12Q 1/6827* (2013.01); *G16H 50/30* (2018.01); *G16B 10/00* (2019.02)

(58) Field of Classification Search
None
See application file for complete search history.

(56) References Cited

U.S. PATENT DOCUMENTS

| | | | |
|---|---|---|---|
| 8,543,339 B2 | 9/2013 | Wojcicki et al. | |
| 2002/0077775 A1* | 6/2002 | Schork | G16B 30/00 702/179 |
| 2003/0195707 A1* | 10/2003 | Schork | G16B 20/00 702/20 |
| 2005/0112684 A1 | 5/2005 | Holzle | |
| 2005/0278125 A1* | 12/2005 | Harwood | G06Q 50/10 702/20 |
| 2009/0099789 A1* | 4/2009 | Stephan | G16B 20/00 702/20 |
| 2009/0162348 A1 | 6/2009 | Li et al. | |
| 2009/0299645 A1 | 12/2009 | Colby et al. | |
| 2010/0022406 A1 | 1/2010 | Srinivasan et al. | |

FOREIGN PATENT DOCUMENTS

| | | |
|---|---|---|
| EP | 1962212 | 8/2008 |
| WO | WO2004/092333 | 10/2004 |
| WO | WO2008/087185 | 7/2008 |
| WO | WO 2009/117122 A2 | 9/2009 |
| WO | WO 2011/038155 A2 | 3/2011 |

OTHER PUBLICATIONS

Nield (Google's Quantum Computer is 100 Million Times Faster Than Your Laptop; 2015, pp. 1-5) (Year: 2015).*
European Search Report Issued for European Patent Application No. 10825601.7, dated Sep. 18, 2014.
Li, et al., "Generating Samples for Association Studies Based on HapMap Data", BioMed Central, BMC Bioinformatics, Jan. 24, 2008, pp. 1-13.
International Search Report and Written Opinion issued for corresponding PCT International Patent Application No. PCT/US2010/053396, dated Mar. 23, 2011.
Baskovich et al. "Expanded genetic screening panel for the Ashkenazi Jewish population", Genetics in Medicine, 2016, vol. 18, No. 5, pp. 522-528.
Silver et al. "Carrier Screening is a Deficient Strategy for Determining Sperm Donor Eligibility and Reducing Risk of Disease in Recipient Children", Genetic Testing and Molecular Biomarkers, 2016, vol. 20, No. 6, pp. 276-284.
Srinivasan et al. "A universal carrier test for the long tail of Mendelian disease", Reproductive BioMedicine Online, 2010, pp. 537-551.
Burke et al. "Genetic Screening", Epidemiologic Reviews, Jun. 27, 2011, vol. 33, pp. 148-164.
Callum et al. "Spinal muscular atrophy (SMA) after conception using gametes from anonymous donors: recommendations for the future", Fertility and Sterility, Feb. 2010, vol. 93, No. 93, pp. 1006.e1-1006.e2.
Eypasch et al. "Probability of adverse events that have not yet occurred: a statistical reminder", Fertility and Sterility, Sep. 2, 1995, vol. 311, No. 93, pp. 619-620.
Green et al. "Psychosocial aspects of genetic screening of pregnant women and newborns: a systematic review", Health Technology Assessment, 2004, vol. 8, No. 33, pp. 1-4.
Levenson, "Genetic discrimination lawsuit raises broader concerns about testing, privacy", American Journal of Medical Genetics, 2016, pp. 1111-1112.
Martin et al. "Comprehensive carrier genetic test using next-generation deoxyribonucleic acid sequencing in infertile couples wishing to conceive through assisted reproductive technology", Fertility and Sterility, Nov. 2015, vol. 104, No. 5, pp. 1286-1293.
Larson et al., "Validation of a high resolution NGS method for detecting spinal muscular atrophy carriers among phase 3 participants in the 1000 Genomes Project", BMC Medical Genetics, (2015), 16:100, pp. 1-14.
Picard Tools, Broad Institute, https://broadinstitute.github.io/picard/ ; printed on Mar. 14, 2017.
SAMtools, GitHub Social Coding http://samtools.sourceforge.net/ , Last Modified: Sep. 12, 2012.
Wiki, Snakemake/Documentation http://snakemake.readthedocs.io/en/stable/ ; 2014-2016.

(Continued)

*Primary Examiner* — Pablo S Whaley
(74) *Attorney, Agent, or Firm* — Fenwick & West LLP

(57) ABSTRACT

Methods and systems for assessing the probabilities of the expression of one or more traits in progeny are described.

20 Claims, 16 Drawing Sheets

Specification includes a Sequence Listing.

(56) References Cited

OTHER PUBLICATIONS

View Run & Lane Metrics, Illumina, BaseSpace Online Help https://support.Illumina.com/help/BaseSpace_OLH_009008/Content/Vault/Informatics/Sequencing_Analysis/BS/swSEQ_mBS_ViewRunSamplesList.htm; printed on Mar. 14, 2017.
The Variant Call Format (VCF) Version 4.2 Specification, Nov. 15, 2016, https://github.com/samtools/hts-specs, pp. 1-28.
GenePeeks, Inc., GitHub, Inc. [US], https://github.com/GenePeeks; printed on Mar. 14, 2017.
Data Protection, Amazon Web Services, https://aws.amazon.com/s3/faqs/#data-protection; printed on Mar. 14, 2017.
Burrows—Wheeler Aligner http://bio-bwa.sourceforge.net/, Last Modified: Feb. 28, 2010.
Amazon EC2 Instance Types, Amazon Web Services https://aws.amazon.com/ec2/instance-types/; printed on Mar. 14, 2017.
Reads-to-variants workflows used at the Broad Institute, GATK Best Practices, Recommended workflows for variant discovery analysis with GATK, GATK https://software.broadinstitute.org/gatk/best-practices/; printed on Mar. 14, 2017.
GregoryFaust/samblaster, GitHub, Inc. [US] https://github.com/GregoryFaust/samblaster , Published on May 7, 2014.
HaplotypeCaller, Call germline SNPs and indels via local re-assembly of haplotypes, GATK https://software.broadinstitute.org/gatk/documentation/tooldocs/current/org_broadinstitute_gatk_tools_walkers_haplotypecaller_haplotypecaller.php; Feb. 9, 2017.
Resource at: https://support.illumina.com/content/dam/illumina-support/documents/downloads/software/bcl2fastq/bcl2fastq2-v2-18-software-guide-15051736-01.pdf; Apr. 2016.
BaseRecalibrator, Detect systematic errors in base quality scores, GATK Best Practices, GATK, https://software.broadinstitute.org/gatk/documentation/tooldocs/current/org_broadinstitute_gatk_tools_walkers_bqsr_BaseRecalibrator.php; Jul. 29, 2017.
MongoDB Documentation https://docs.mongodb.com/?_ga=1.52591065.459598860.1467921146; Jul. 26, 2017.
HaplotypeCaller https://software.broadinstitute.org/getk/documentation/tooldocs/current/org_broadinstitute_gatk_tools_walkers_haplotypecaller_HaplotypeCaller.php; Jul. 29, 2017.
Genome Profile DataBase http://gpdb.life.nthu.edu.tw/GPDB/index.php ; 2006.
United States Office Action, U.S. Appl. No. 13/591,373, Jun. 6, 2013, 13 pages.
United States Office Action, U.S. Appl. No. 12/908,636, Jun. 10, 2013, 13 pages.

* cited by examiner

| LOCUS> | 01 | 02 | 03 | 04 | 05 | C | T | 06 | ... | N |
|---|---|---|---|---|---|---|---|---|---|---|
| John Smith | A | T | G | G | C | 0.3 | 0.7 | C | ... | A |
| | C | T | C | C | A | 0.7 | 0.3 | T | ... | T |
| Jane Doe | A | A | C | C | A | 0.5 | 0.5 | C | ... | A |
| | A | A | C | C | A | 0.5 | 0.5 | T | ... | A |

↑ ↑

| LOCUS> | 01 | 02 | 03 | 04 | 05 | 06 | ... | N |
|---|---|---|---|---|---|---|---|---|
| John Smith | AC | | CG | | | TT | ... | AT |
| Jane Doe | AA | | CC | | | TC | ... | AA |

Haplopath 1

| LOCUS> | 01 | 02 | 03 | 04 | 05 | C | T | 06 | .... | N |
|---|---|---|---|---|---|---|---|---|---|---|
| John Smith | A | T | G | C | C | 0.3 | 0.7 | C | .... | A |
| | C | T | C | C | A | 0.7 | 0.3 | T | .... | T |

Haplopath 7

| LOCUS> | 01 | 02 | 03 | 04 | 05 | C | T | 06 | .... | N |
|---|---|---|---|---|---|---|---|---|---|---|
| John Smith | A | T | G | G | C | 0.3 | 0.7 | C | .... | A |
| | C | T | C | C | A | 0.7 | 0.3 | T | .... | T |

Each individual genome profile is used to generate a pool of VirtualGametes.

FIG. 4

| Genotype | number of possible genotypes | code | Partner#1 | Partner#2 | Partner#3 | Partner#4 |
|---|---|---|---|---|---|---|
| DD | 1 | 0 | 105,868 | 16,638 | 59,094 | 19,360 |
| AD,DD | 2 | 0.5 | 120,160 | 35,607 | 76,215 | 20,746 |
| AD | 1 | 1 | 54,454 | 24,342 | 36,079 | 69,948 |
| AD,AA | 2 | 1.5 | 199,886 | 70,411 | 129,133 | 79,562 |
| AA | 1 | 2 | 373,011 | 59,965 | 163,821 | 107,123 |
| DD,AD,AA | 3 | 5 | 100,102 | 31,206 | 63,242 | 1,716 |
| TOTAL SNPs | | | 953,481 | 238,169 | 527,584 | 298,455 |

FIG. 5A

| Total | Disease or Trait | Informative SNPs | SNP ID | partner #1 | partner #2 | partner #3 | partner #4 |
|---|---|---|---|---|---|---|---|
| 1 | Age at natural menopause | 1 | rs291353 | 1.5 | 5 | 1.5 | 1.5 |
| 2 | Alkaline phosphatase | 1 | rs10518765 | 2 | 2 | 1.5 | 2 |
| 3 | Ankle brachial index | 1 | rs10505346 | 5 | 5 | 1.5 | 1.5 |
| 4 | Arterial Stiffness | 1 | rs10511389 | 2 | 1.5 | 2 | 2 |
| 5 | Asthma | 1 | rs2290400 | 1 | 0.5 | 1 | 1 |
| 6 | Cardiac repolarization | 1 | rs2160512 | 1.5 | 2 | 1 | 2 |
| 7 | Diabetes, Type II survival | 1 | rs861085 | 1 | 0 | 0.5 | 1 |
| 8 | Exfoliation glaucoma | 1 | rs2165241 | 0.5 | 5 | 0.5 | 5 |
| 9 | Glaucoma | 1 | rs10152898 | 0 | 0 | 1 | 1 |
| 10 | Glucose tolerance test | 1 | rs2540317 | 1.5 | 2 | 2 | 2 |
| 11 | Heart rate variability | 5 | rs9297393 | 0.5 | 5 | 5 | 1.5 |
| 12 | Heart rate variability | 5 | rs10516736 | 2 | 2 | 2 | 2 |
| 13 | Heart rate variability | 5 | rs1932933 | 1 | 2 | 1.5 | 2 |
| 14 | Heart rate variability | 5 | rs9291683 | 1.5 | 1.5 | 1 | 2 |
| 15 | Heart rate variability | 5 | rs6063312 | 5 | 5 | 1.5 | 1.5 |
| 16 | Hematocrit | 1 | rs9285468 | 1.5 | 2 | 1.5 | 2 |
| 17 | Hip geometry | 2 | rs2008691 | 0 | 0.5 | 0.5 | 1 |
| 18 | Hip geometry | 2 | rs1395548 | 0 | 1 | 0.5 | 1 |
| 19 | Intracellular adhesion molecule | 1 | rs744511 | 1.5 | 2 | 2 | 1 |
| 20 | Ischemic stroke | 1 | rs7043482 | 1.5 | 5 | 1.5 | 0.5 |
| 21 | MCH;0.000000069 | 1 | rs1397048 | 0.5 | 5 | 0.5 | 1.5 |
| 22 | meanfvc;0.00000978 | 1 | rs156697 | 1.5 | 1 | 1 | 2 |
| 23 | meanratio;0.008 | 1 | rs10483190 | 2 | 1.5 | 2 | 2 |
| 24 | Morbidity-free survival at age 65 | 1 | rs10500784 | 2 | 2 | 1.5 | 2 |
| 25 | Myocardial infarction | 1 | rs4977574 | 0.5 | 0.5 | 0.5 | 1 |
| 26 | Neuroticism | 1 | rs873989 | 5 | 5 | 5 | 1.5 |
| 27 | platelet aggregation (collagen induced) | 1 | rs848523 | 5 | 5 | 0.5 | 5 |
| 28 | platelet aggregation (Epi induced) | 1 | rs10502583 | 2 | 2 | 2 | 2 |
| 29 | Population differentiation markers | 1 | rs7696175 | 2 | 2 | 1.5 | 2 |
| 30 | Red blood cell count | 1 | rs6108011 | 2 | 2 | 1.5 | 2 |
| 31 | Serum uric acid levels | 1 | rs6449213 | 5 | 1.5 | 1.5 | 1.5 |
| 32 | Trochanter Bone Mineral Density | 1 | rs10510628 | 1 | 2 | 1.5 | 2 |
| 33 | UAE;4.10E-05 | 1 | rs2761171 | 1.5 | 0.5 | 5 | 1.5 |
| 34 | Combined Bone Mineral Density | 2 | rs8051539 | 1.5 | 2 | 2 | 2 |
| 35 | Combined Bone Mineral Density pheno | 2 | rs181224 | 5 | 5 | 5 | 1.5 |
| 36 | Childhood asthma | 3 | rs2037986 | 0 | 1 | 0 | 1 |
| 37 | Childhood asthma | 3 | rs8066582 | 0.5 | 0.5 | 0.5 | 0 |
| 38 | Restless Leg Syndrome | 3 | rs12593813 | 5 | 5 | 0.5 | 1.5 |
| 39 | Restless Leg Syndrome | 3 | rs3784709 | 5 | 5 | 0.5 | 1.5 |

FIG. 5B

| Total | Disease or Trait | Informative SNPs | SNP ID | partner #1 | partner #2 | partner #3 | partner #4 |
|---|---|---|---|---|---|---|---|
| 40 | Sporadic post-menopausal breast cancer | 3 | rs7696175 | 2 | 2 | 1.5 | 2 |
| 41 | Sporadic post-menopausal breast cancer | 3 | rs1219648 | 1.5 | 2 | 1 | 1 |
| 42 | Stroke | 3 | rs2935718 | 0.5 | 1.5 | 0.5 | 1.5 |
| 43 | Stroke | 3 | rs10511679 | 1.5 | 1 | 2 | 2 |
| 44 | tFPG | 3 | rs7147624 | 1.5 | 2 | 1.5 | 2 |
| 45 | tFPG | 3 | rs10496802 | 2 | 2 | 2 | 2 |
| 46 | C-reactive protein | 4 | rs583012 | 2 | 1.5 | 2 | 2 |
| 47 | C-reactive protein | 4 | rs2794520 | 1.5 | 2 | 1.5 | 2 |
| 48 | C-reactive protein | 4 | rs1363258 | 1.5 | 1.5 | 5 | 1.5 |
| 49 | Hip circumference | 4 | rs1421085 | 1 | 1 | 0 | 1 |
| 50 | Hip circumference | 4 | rs5758108 | 2 | 2 | 2 | 2 |
| 51 | Hip circumference | 4 | rs8050136 | 1 | 1.5 | 2 | 1 |
| 52 | Immunological resistance IL-6a | 4 | rs698270 | 0.5 | 0.5 | 1 | 1 |
| 53 | Immunological resistance IL-6a | 4 | rs1436136 | 1 | 1 | 1 | 1 |
| 54 | Immunological resistance IL-6a | 4 | rs10503717 | 5 | 1.5 | 1.5 | 1.5 |
| 55 | Large vessel stroke | 4 | rs2838046 | 1.5 | 1.5 | 2 | 2 |
| 56 | Large vessel stroke | 4 | rs11195266 | 2 | 2 | 1 | 2 |
| 57 | Large vessel stroke | 4 | rs534654 | 2 | 1.5 | 2 | 2 |
| 58 | Polysubstance addiction | 4 | rs2822985 | 0 | 0 | 0.5 | 1 |
| 59 | Polysubstance addiction | 4 | rs164006 | 2 | 2 | 2 | 2 |
| 60 | Polysubstance addiction | 4 | rs7539409 | 2 | 2 | 2 | 2 |
| 61 | ppfef | 4 | rs10498441 | 0 | 0 | 1 | 1 |
| 62 | ppfef | 4 | rs808225 | 1 | 2 | 1.5 | 2 |
| 63 | ppfef | 4 | rs880713 | 1.5 | 2 | 1.5 | 2 |
| 64 | Small vessel stroke | 4 | rs911979 | 1 | 2 | 2 | 2 |
| 65 | breast cancer and prostate cancer | 5 | rs6691482 | 0 | 0.5 | 1 | 0 |
| 66 | breast cancer and prostate cancer | 5 | rs2274626 | 0.5 | 0.5 | 1 | 0 |
| 67 | breast cancer and prostate cancer | 5 | rs1926657 | 0.5 | 1.5 | 1.5 | 1.5 |
| 68 | breast cancer and prostate cancer | 5 | rs1562871 | 2 | 1.5 | 2 | 2 |
| 69 | End stage renal disease | 5 | rs2720662 | 1 | 0 | 0.5 | 0 |
| 70 | End stage renal disease | 5 | rs2720659 | 1.5 | 1.5 | 5 | 1.5 |
| 71 | End stage renal disease | 5 | rs2720709 | 1.5 | 5 | 5 | 1.5 |
| 72 | End stage renal disease | 5 | rs2648876 | 1.5 | 1.5 | 1.5 | 1.5 |
| 73 | Episodic memory | 5 | rs7549870 | 0.5 | 5 | 5 | 1.5 |
| 74 | Episodic memory | 5 | rs9660884 | 5 | 0.5 | 1.5 | 1.5 |
| 75 | Episodic memory | 5 | rs1011126 | 0.5 | 1.5 | 0.5 | 1.5 |
| 76 | Episodic memory | 5 | rs7547519 | 1.5 | 5 | 5 | 0.5 |
| 77 | Heart Failure | 5 | rs752876 | 0 | 0.5 | 0 | 1 |
| 78 | Heart Failure | 5 | rs1176486 | 5 | 1.5 | 1.5 | 1.5 |
| 79 | Heart Failure | 5 | rs10515869 | 0 | 0.5 | 1 | 1 |
| 80 | Heart Failure | 5 | rs740363 | 0.5 | 0.5 | 0 | 0 |

FIG. 5C

| Total | Disease or Trait | Informative SNPs | SNP ID | partner #1 | partner #2 | partner #3 | partner #4 |
|---|---|---|---|---|---|---|---|
| 81 | MRI and cognition phenotypes | 5 | rs1822285 | 1.5 | 1.5 | 1 | 2 |
| 82 | MRI and cognition phenotypes | 5 | rs1970546 | 1.5 | 1.5 | 1.5 | 1.5 |
| 83 | MRI and cognition phenotypes | 5 | rs1155865 | 0 | 0.5 | 0.5 | 0 |
| 84 | MRI and cognition phenotypes | 5 | rs1831521 | 1 | 0 | 0.5 | 1 |
| 85 | Skin pigmentation | 5 | rs10519193 | 0.5 | 1 | 0.5 | 1 |
| 86 | Diabetes, Type II in non-obese | 6 | rs12255372 | 1 | 0 | 1 | 1 |
| 87 | Diabetes, Type II in non-obese | 6 | rs2191113 | 0.5 | 1 | 1 | 1 |
| 88 | Diabetes, Type II in non-obese | 6 | rs10502860 | 0.5 | 0 | 0.5 | 0 |
| 89 | Diabetes, Type II in non-obese | 6 | rs2170862 | 1.5 | 1.5 | 2 | 2 |
| 90 | Diabetes, Type II in non-obese | 6 | rs10483957 | 0.5 | 1.5 | 1.5 | 1.5 |
| 91 | Prostate cancer | 6 | rs6083025 | 1.5 | 1.5 | 1.5 | 1 |
| 92 | Prostate cancer | 6 | rs6983267 | 5 | 5 | 0.5 | 1.5 |
| 93 | Prostate cancer | 6 | rs13149290 | 1.5 | 5 | 5 | 0.5 |
| 94 | Prostate cancer | 6 | rs1545985 | 0.5 | 5 | 5 | 1.5 |
| 95 | Prostate cancer | 6 | rs629242 | 1.5 | 2 | 2 | 2 |
| 96 | Breast cancer | 7 | rs6463266 | 1.5 | 1.5 | 2 | 1 |
| 97 | Breast cancer | 7 | rs7307700 | 1.5 | 1 | 2 | 2 |
| 98 | Breast cancer | 7 | rs3803662 | 1.5 | 1.5 | 1.5 | 2 |
| 99 | Breast cancer | 7 | rs2981582 | 1.5 | 1.5 | 1 | 1 |
| 100 | Breast cancer | 7 | rs9956546 | 2 | 2 | 2 | 2 |
| 101 | Breast cancer | 7 | rs3803662 | 1.5 | 1.5 | 1.5 | 2 |
| 102 | ISI_0-120.t | 7 | rs152608 | 1.5 | 1.5 | 1.5 | 2 |
| 103 | ISI_0-120.t | 7 | rs4895477 | 1.5 | 1.5 | 1.5 | 1.5 |
| 104 | ISI_0-120.t | 7 | rs10491899 | 2 | 2 | 2 | 2 |
| 105 | ISI_0-120.t | 7 | rs4558292 | 1.5 | 1 | 1.5 | 2 |
| 106 | ISI_0-120.t | 7 | rs755011 | 2 | 1.5 | 1.5 | 2 |
| 107 | ISI_0-120.t | 7 | rs10503835 | 1.5 | 2 | 2 | 2 |
| 108 | Amyotrophic Lateral Sclerosis (Early Onset) | 8 | rs1390762 | 2 | 1 | 2 | 2 |
| 109 | Amyotrophic Lateral Sclerosis (Early Onset) | 8 | rs11096490 | 2 | 1.5 | 2 | 2 |
| 110 | Amyotrophic Lateral Sclerosis (Early Onset) | 8 | rs1326022 | 1.5 | 2 | 1.5 | 2 |
| 111 | Amyotrophic Lateral Sclerosis (Early Onset) | 8 | rs1799898 | 2 | 2 | 2 | 2 |
| 112 | Amyotrophic Lateral Sclerosis (Early Onset) | 8 | rs2400707 | 1.5 | 1 | 1.5 | 1 |
| 113 | Amyotrophic Lateral Sclerosis (Early Onset) | 8 | rs1922531 | 5 | 5 | 5 | 0.5 |
| 114 | Amyotrophic Lateral Sclerosis (Early Onset) | 8 | rs17763104 | 2 | 2 | 2 | 2 |
| 115 | Celiac disease | 8 | rs4571541 | 1.5 | 5 | 1.5 | 1.5 |

FIG. 5D

| Total | Disease or Trait | Informative SNPs | SNP ID | partner #1 | partner #2 | partner #3 | partner #4 |
|---|---|---|---|---|---|---|---|
| 116 | Celiac disease | 8 | rs1021621 | 1 | 2 | 1 | 2 |
| 117 | Celiac disease | 8 | rs7708940 | 1.5 | 1 | 2 | 1 |
| 118 | Celiac disease | 8 | rs3809973 | 0.5 | 1 | 1 | 1 |
| 119 | Celiac disease | 8 | rs200755 | 1.5 | 5 | 0.5 | 1.5 |
| 120 | Celiac disease | 8 | rs3949904 | 0.5 | 0.5 | 5 | 1.5 |
| 121 | Celiac disease | 8 | rs13357969 | 0.5 | 0.5 | 0 | 1 |
| 122 | eye and skin pigmentation | 8 | rs1042602 | 0.5 | 5 | 0.5 | 1.5 |
| 123 | eye and skin pigmentation | 8 | rs2402130 | 0.5 | 1.5 | 5 | 1.5 |
| 124 | eye and skin pigmentation | 8 | rs8039195 | 0.5 | 0.5 | 0 | 1 |
| 125 | eye and skin pigmentation | 8 | rs2353033 | 0.5 | 0 | 0.5 | 0 |
| 126 | eye and skin pigmentation | 8 | rs7188458 | 1.5 | 5 | 0.5 | 1.5 |
| 127 | eye and skin pigmentation | 8 | rs258322 | 2 | 2 | 1.5 | 1 |
| 128 | eye and skin pigmentation | 8 | rs4238833 | 1.5 | 1 | 2 | 2 |
| 129 | HbA1c | 8 | rs6021247 | 2 | 1.5 | 1.5 | 2 |
| 130 | HbA1c | 8 | rs2778 | 0.5 | 5 | 1.5 | 1.5 |
| 131 | HbA1c | 8 | rs9302427 | 0 | 1 | 0.5 | 0 |
| 132 | HbA1c | 8 | rs7937934 | 0.5 | 0.5 | 0 | 1 |
| 133 | HbA1c | 8 | rs10483891 | 2 | 2 | 2 | 2 |
| 134 | HbA1c | 8 | rs1892432 | 1.5 | 5 | 1.5 | 1.5 |
| 135 | HbA1c | 8 | rs9297181 | 1.5 | 5 | 1.5 | 1.5 |
| 136 | mFPG | 8 | rs2222514 | 1.5 | 1.5 | 1.5 | 2 |
| 137 | mFPG | 8 | rs285322 | 0.5 | 5 | 0.5 | 0.5 |
| 138 | mFPG | 8 | rs3904063 | 1.5 | 1.5 | 1.5 | 1.5 |
| 139 | mFPG | 8 | rs1446750 | 1.5 | 1.5 | 2 | 2 |
| 140 | mFPG | 8 | rs8138344 | 0.5 | 5 | 0.5 | 1.5 |
| 141 | mFPG | 8 | rs10516339 | 5 | 1.5 | 1.5 | 1.5 |
| 142 | mFPG | 8 | rs2258175 | 1.5 | 5 | 0.5 | 1.5 |
| 143 | Nicotine dependence | 8 | rs9630453 | 1 | 2 | 2 | 1.5 |
| 144 | Nicotine dependence | 8 | rs17019859 | 2 | 1.5 | 1.5 | 2 |
| 145 | Nicotine dependence | 8 | rs1491377 | 5 | 5 | 0.5 | 1.5 |
| 146 | Nicotine dependence | 8 | rs7753810 | 1.5 | 5 | 1.5 | 0.5 |
| 147 | Nicotine dependence | 8 | rs1532010 | 2 | 1 | 2 | 2 |
| 148 | Nicotine dependence | 8 | rs2283029 | 2 | 2 | 2 | 2 |
| 149 | Nicotine dependence | 8 | rs1417056 | 5 | 5 | 5 | 1.5 |
| 150 | Sporadic Amyotrophic Lateral Scleros | 8 | rs7531917 | 5 | 1.5 | 5 | 1.5 |
| 151 | brachial artery endothelial functio | 9 | rs10493389 | 0.5 | 5 | 1.5 | 1.5 |
| 152 | brachial artery endothelial functio | 9 | rs4345919 | 2 | 2 | 2 | 2 |
| 153 | brachial artery endothelial functio | 9 | rs180935 | 1.5 | 5 | 0.5 | 1.5 |
| 154 | brachial artery endothelial functio | 9 | rs721575 | 5 | 1.5 | 1.5 | 1.5 |
| 155 | brachial artery endothelial functio | 9 | rs1488745 | 1 | 1.5 | 2 | 2 |
| 156 | brachial artery endothelial functio | 9 | rs10510677 | 2 | 1.5 | 2 | 2 |

FIG. 5E

| Total | Disease or Trait | Informative SNPs | SNP ID | partner #1 | partner #2 | partner #3 | partner #4 |
|---|---|---|---|---|---|---|---|
| 157 | brachial artery endothelial functio | 9 | rs1029946 | 0.5 | 1 | 0 | 0 |
| 158 | brachial artery endothelial functio | 9 | rs10491574 | 2 | 1 | 1.5 | 2 |
| 159 | Colorectal cancer | 10 | rs910315 | 2 | 2 | 2 | 2 |
| 160 | Colorectal cancer | 10 | rs1454027 | 2 | 1.5 | 1.5 | 2 |
| 161 | Colorectal cancer | 10 | rs10484791 | 5 | 5 | 5 | 1.5 |
| 162 | Colorectal cancer | 10 | rs9328033 | 1.5 | 2 | 1.5 | 1 |
| 163 | Colorectal cancer | 10 | rs9297758 | 1.5 | 1.5 | 1.5 | 2 |
| 164 | Colorectal cancer | 10 | rs6999921 | 0 | 0 | 0 | 0 |
| 165 | Colorectal cancer | 10 | rs6470494 | 5 | 0.5 | 1.5 | 1.5 |
| 166 | Colorectal cancer | 10 | rs6983267 | 5 | 5 | 0.5 | 1.5 |
| 167 | Colorectal cancer | 10 | rs6983267 | 5 | 5 | 0.5 | 1.5 |
| 168 | FPG | 10 | rs958380 | 2 | 2 | 2 | 2 |
| 169 | FPG | 10 | rs980238 | 1.5 | 2 | 2 | 2 |
| 170 | FPG | 10 | rs4509878 | 5 | 0.5 | 0.5 | 0.5 |
| 171 | FPG | 10 | rs1276535 | 1.5 | 1.5 | 1 | 2 |
| 172 | FPG | 10 | rs4419819 | 1 | 1 | 0.5 | 1 |
| 173 | FPG | 10 | rs1998623 | 1.5 | 1.5 | 5 | 0.5 |
| 174 | FPG | 10 | rs1567700 | 1.5 | 1.5 | 1.5 | 1.5 |
| 175 | FPG | 10 | rs973391 | 1.5 | 5 | 5 | 0.5 |
| 176 | FPG | 10 | rs6664618 | 1.5 | 1.5 | 5 | 1.5 |
| 187 | Diabetes, Early onset, Type II | 11 | | | | | |
| 204 | Gallstone disease | 17 | | | | | |
| 223 | Multiple sclerosis | 19 | | | | | |
| 244 | Systolic Blood Pressure | 21 | | | | | |
| 268 | Triglyceride/HDL ratio | 24 | | | | | |
| 293 | Fasting glucose | 25 | | | | | |
| 318 | Total cholesterol | 25 | | | | | |
| 343 | Waist/height ratio | 25 | | | | | |
| 369 | ApoA-I | 26 | | | | | |
| 396 | ApoAII | 27 | | | | | |
| 424 | Fat mass | 28 | | | | | |
| 452 | LDL cholesterol | 28 | | | | | |
| 482 | ApoB | 30 | | | | | |
| 513 | HOMA-IR | 31 | | | | | |
| 544 | Insulin response | 31 | | | | | |
| 578 | Diastolic Blood Pressure | 34 | | | | | |
| 613 | HDL cholesterol | 35 | | | | | |
| 652 | Fasting insulin | 39 | | | | | |
| 696 | Triglycerides | 44 | | | | | |

FIG. 5F

| Total | Disease or Trait | Informative SNPs | SNP ID | partner #1 | partner #2 | partner #3 | partner #4 |
|---|---|---|---|---|---|---|---|
| 742 | Diabetes Mellitus | 46 | | | | | |
| 793 | Height | 51 | | | | | |
| 846 | Waist circumference | 53 | | | | | |
| 901 | Weight | 55 | | | | | |
| 959 | Waist/hip ratio | 58 | | | | | |
| 1,018 | HIV-1 viral load at set point | 59 | | | | | |
| 1,091 | Body Mass Index | 73 | | | | | |
| 1,200 | Parkinson's disease | 109 | | | | | |
| 1,367 | Rheumatoid Arthritis | 167 | | | | | |
| 1,535 | Alzheimer's disease | 168 | | | | | |
| 1,731 | Hypertension | 196 | | | | | |
| 1,947 | Amyotrophic Lateral Sclerosis (ALS) | 216 | | | | | |
| 2,176 | Bipolar disorder | 229 | | | | | |
| 2,414 | Coronary Artery Disease | 238 | | | | | |
| 2,661 | Crohn's disease | 247 | | | | | |
| 2,926 | Diabetes, Type I | 265 | | | | | |
| 3,254 | Diabetes, Type II | 328 | | | | | |

FIG. 6A

|     | 1 | 2 | 3 | 4 | 5 | 6 | 7 | 8 | 9 |
|-----|---|---|---|---|---|---|---|---|---|
|     | 64 | 65 | 66 | 67 | 68 | 69 | 70 | 71 | 72 |
| H1  | 0 | 0 | 1 | 0 | 0 | 0 | 1 | 1 | 0 |
| H2  | 0 | 1 | 0 | 0 | 0 | 1 | 1 | 0 | 0 |
| H3  | 1 | 0 | 1 | 0 | 1 | 0 | 0 | 0 | 1 |
| H4  | 0 | 1 | 0 | 1 | 0 | 0 | 0 | 0 | 0 |
| H5  | 1 | 0 | 0 | 0 | 0 | 0 | 0 | 0 | 0 |
| H6  | 1 | 0 | 0 | 0 | 0 | 0 | 0 | 1 | 0 |
| H7  | 1 | 0 | 1 | 1 | 0 | 0 | 0 | 0 | 0 |
| H8  | 0 | 1 | 0 | 0 | 0 | 1 | 1 | 1 | 0 |
| H9  | 0 | 0 | 0 | 1 | 0 | 0 | 1 | 0 | 1 |
| H10 | 0 | 1 | 0 | 1 | 1 | 0 | 1 | 0 | 0 |
| H11 | 0 | 1 | 1 | 0 | 0 | 0 | 0 | 0 | 1 |
| H12 | 0 | 0 | 1 | 0 | 0 | 0 | 1 | 1 | 1 |
| H13 | 1 | 1 | 0 | 1 | 0 | 0 | 0 | 0 | 1 |
| H14 | 0 | 1 | 1 | 0 | 0 | 0 | 1 | 0 | 1 |
| H15 | 0 | 0 | 0 | 0 | 1 | 0 | 0 | 0 | 0 |
| H16 | 0 | 0 | 0 | 0 | 0 | 1 | 1 | 0 | 1 |
| H17 | 0 | 0 | 0 | 1 | 0 | 0 | 1 | 0 | 1 |
| H18 | 1 | 0 | 1 | 0 | 0 | 0 | 0 | 0 | 0 |
| H19 | 0 | 0 | 1 | 0 | 1 | 0 | 0 | 1 | 0 |
| H20 | 1 | 0 | 0 | 1 | 0 | 0 | 1 | 0 | 0 |
| H21 | 0 | 0 | 0 | 0 | 0 | 1 | 0 | 1 | 0 |
| H22 | 1 | 0 | 0 | 1 | 0 | 1 | 0 | 0 | 1 |
| H23 | 1 | 1 | 0 | 1 | 1 | 1 | 0 | 0 | 0 |
| H24 | 0 | 0 | 0 | 0 | 0 | 0 | 1 | 1 | 0 |
| H25 | 1 | 0 | 0 | 0 | 0 | 0 | 1 | 0 | 0 |
| H26 | 0 | 0 | 1 | 0 | 0 | 0 | 1 | 0 | 0 |
| H27 | 0 | 0 | 0 | 0 | 0 | 0 | 1 | 1 | 0 |
| H28 | 1 | 0 | 1 | 0 | 0 | 0 | 1 | 0 | 0 |
| H29 | 0 | 0 | 0 | 1 | 1 | 0 | 0 | 1 | 1 |
| H30 | 1 | 1 | 1 | 1 | 1 | 0 | 1 | 1 | 0 |
| H31 | 0 | 0 | 0 | 0 | 0 | 0 | 1 | 1 | 1 |
| H32 | 0 | 1 | 0 | 0 | 1 | 0 | 1 | 1 | 1 |
| H33 | 1 | 1 | 0 | 0 | 0 | 0 | 0 | 0 | 0 |
| H34 | 1 | 1 | 0 | 1 | 0 | 1 | 1 | 0 | 1 |
| H35 | 0 | 0 | 0 | 0 | 0 | 1 | 0 | 0 | 1 |
| H36 | 0 | 0 | 0 | 1 | 0 | 1 | 0 | 0 | 1 |
| H37 | 0 | 1 | 1 | 0 | 1 | 1 | 1 | 0 | 0 |
| H38 | 1 | 1 | 0 | 0 | 0 | 0 | 0 | 0 | 0 |
| H39 | 1 | 1 | 0 | 1 | 1 | 0 | 0 | 1 | 0 |
| H40 | 1 | 1 | 0 | 0 | 1 | 0 | 1 | 0 | 0 |
| H41 | 1 | 0 | 0 | 0 | 1 | 0 | 1 | 1 | 0 |
| H42 | 1 | 1 | 0 | 1 | 0 | 0 | 0 | 0 | 0 |
| H43 | 0 | 0 | 0 | 0 | 0 | 0 | 0 | 1 | 1 |
| H44 | 0 | 0 | 1 | 0 | 0 | 1 | 1 | 0 | 1 |
| H45 | 0 | 1 | 0 | 1 | 0 | 0 | 0 | 0 | 0 |
| H46 | 0 | 1 | 1 | 0 | 1 | 0 | 0 | 0 | 0 |
| H47 | 1 | 0 | 0 | 1 | 1 | 0 | 0 | 1 | 0 |
| H48 | 1 | 0 | 0 | 1 | 0 | 1 | 0 | 0 | 0 |
| H49 | 1 | 0 | 1 | 1 | 0 | 0 | 0 | 0 | 0 |

FIG. 6B

|  | 1 | 2 | 3 | 4 | 5 | 6 | 7 | 8 | 9 |
|---|---|---|---|---|---|---|---|---|---|
|  | 64 | 65 | 66 | 67 | 68 | 69 | 70 | 71 | 72 |
| H50 | 0 | 0 | 0 | 0 | 1 | 1 | 0 | 1 | 0 |
| H51 | 0 | 0 | 1 | 0 | 0 | 1 | 1 | 1 | 0 |
| H52 | 1 | 0 | 0 | 0 | 0 | 0 | 0 | 0 | 0 |
| H53 | 0 | 0 | 0 | 1 | 0 | 1 | 0 | 1 | 0 |
| H54 | 0 | 0 | 0 | 1 | 1 | 0 | 0 | 1 | 0 |
| H55 | 1 | 0 | 0 | 0 | 0 | 1 | 1 | 1 | 0 |
| H56 | 0 | 1 | 1 | 0 | 0 | 0 | 1 | 0 | 0 |
| H57 | 0 | 0 | 1 | 0 | 1 | 1 | 0 | 1 | 0 |
| H58 | 0 | 0 | 1 | 1 | 0 | 1 | 0 | 0 | 0 |
| H59 | 1 | 0 | 0 | 1 | 1 | 0 | 1 | 0 | 0 |
| H60 | 1 | 0 | 0 | 1 | 1 | 1 | 0 | 1 | 0 |
| H61 | 0 | 0 | 0 | 1 | 0 | 0 | 1 | 1 | 0 |
| H62 | 1 | 1 | 0 | 1 | 1 | 0 | 0 | 1 | 1 |
| H63 | 0 | 0 | 0 | 0 | 0 | 0 | 0 | 0 | 0 |
| H64 | 1 | 0 | 0 | 1 | 0 | 0 | 0 | 1 | 0 |
| H65 | 0 | 0 | 0 | 0 | 0 | 0 | 0 | 0 | 0 |
| H66 | 0 | 0 | 1 | 0 | 0 | 1 | 0 | 1 | 0 |
| H67 | 1 | 0 | 0 | 1 | 1 | 1 | 0 | 0 | 1 |
| H68 | 0 | 0 | 0 | 0 | 0 | 0 | 0 | 1 | 0 |
| H69 | 0 | 0 | 1 | 0 | 0 | 0 | 0 | 0 | 1 |
| H70 | 0 | 0 | 0 | 0 | 0 | 1 | 0 | 1 | 0 |
| H71 | 1 | 0 | 1 | 0 | 1 | 0 | 1 | 0 | 0 |
| H72 | 1 | 0 | 1 | 0 | 0 | 0 | 0 | 0 | 0 |
| H73 | 0 | 1 | 0 | 1 | 1 | 1 | 0 | 0 | 1 |
| H74 | 0 | 1 | 1 | 0 | 0 | 0 | 1 | 1 | 0 |
| H75 | 1 | 0 | 0 | 1 | 1 | 0 | 1 | 0 | 1 |
| H76 | 1 | 0 | 0 | 1 | 0 | 1 | 0 | 0 | 0 |
| H77 | 1 | 1 | 0 | 1 | 0 | 0 | 0 | 0 | 0 |
| H78 | 0 | 0 | 1 | 1 | 0 | 0 | 0 | 0 | 0 |
| H79 | 1 | 1 | 0 | 0 | 0 | 0 | 0 | 1 | 0 |
| H80 | 1 | 0 | 1 | 1 | 1 | 1 | 1 | 1 | 1 |
| H81 | 0 | 0 | 1 | 0 | 0 | 0 | 0 | 1 | 0 |
| H82 | 1 | 1 | 1 | 1 | 0 | 0 | 0 | 0 | 1 |
| H83 | 0 | 0 | 0 | 1 | 0 | 0 | 0 | 0 | 0 |
| H84 | 0 | 1 | 1 | 0 | 1 | 0 | 1 | 1 | 0 |
| H85 | 0 | 0 | 0 | 0 | 1 | 0 | 1 | 1 | 0 |
| H86 | 1 | 1 | 0 | 1 | 0 | 1 | 1 | 1 | 0 |
| H87 | 0 | 1 | 0 | 0 | 0 | 0 | 0 | 1 | 0 |
| H88 | 0 | 0 | 0 | 1 | 0 | 0 | 1 | 0 | 1 |
| H89 | 1 | 1 | 1 | 1 | 1 | 0 | 0 | 0 | 0 |
| H90 | 1 | 0 | 0 | 0 | 0 | 0 | 0 | 1 | 0 |
| H91 | 1 | 0 | 0 | 1 | 0 | 0 | 0 | 0 | 1 |
| H92 | 0 | 0 | 0 | 0 | 0 | 0 | 1 | 1 | 0 |
| H93 | 0 | 0 | 0 | 0 | 0 | 0 | 1 | 1 | 0 |
| H94 | 1 | 0 | 0 | 1 | 0 | 1 | 0 | 0 | 1 |
| H95 | 1 | 1 | 1 | 0 | 0 | 0 | 1 | 0 | 1 |
| H96 | 1 | 0 | 0 | 1 | 0 | 0 | 0 | 1 | 1 |
| H97 | 1 | 1 | 0 | 1 | 1 | 0 | 0 | 1 | 1 |
| H98 | 1 | 0 | 0 | 1 | 0 | 0 | 0 | 0 | 0 |
| H99 | 0 | 1 | 1 | 1 | 1 | 1 | 0 | 0 | 0 |
| H100 | 0 | 1 | 0 | 0 | 0 | 0 | 1 | 0 | 0 |

SEQUENCE LISTING

<160> NUMBER OF SEQ ID NOS: 6

<210> SEQ ID NO 1
<211> LENGTH: 18
<212> TYPE: DNA
<213> ORGANISM: Homo sapiens

<400> SEQUENCE: 1
cacgcgtgcg gtgcgggc                                                 18

<210> SEQ ID NO 2
<211> LENGTH: 18
<212> TYPE: DNA
<213> ORGANISM: Homo sapiens

```
<400> SEQUENCE: 2
caagcgtgcg atgcgggc                                                  18

<210> SEQ ID NO 3
<211> LENGTH: 18
<212> TYPE: DNA
<213> ORGANISM: Homo sapiens

<400> SEQUENCE: 3
cacgcgtgcg gtacgggc                                                  18

<210> SEQ ID NO 4
<211> LENGTH: 18
<212> TYPE: DNA
<213> ORGANISM: Homo sapiens

<400> SEQUENCE: 4
accatatgtg gcgtatat                                                  18

<210> SEQ ID NO 5
<211> LENGTH: 18
<212> TYPE: DNA
<213> ORGANISM: Homo sapiens

<400> SEQUENCE: 5
cccgcgtgcg gtgtgggc                                                  18

<210> SEQ ID NO 6
<211> LENGTH: 18
<212> TYPE: DNA
<213> ORGANISM: Homo sapiens

<400> SEQUENCE: 6
accgcgcact gtgtgtgc                                                  18
```

METHODS AND SYSTEMS FOR GENERATING A VIRTUAL PROGENY GENOME

CROSS-REFERENCE TO RELATED APPLICATIONS

This application is a continuation of U.S. patent application Ser. No. 12/908,636, filed Oct. 20, 2010, which claims priority to U.S. Provisional Patent Application No. 61/253,108, filed Oct. 20, 2009, each of which is hereby incorporated by reference.

BACKGROUND OF THE INVENTION

In 1866, Mendel described the rules of probability that govern the inheritance of simple genetic traits. He demonstrated that individuals who show no evidence of a disease can still be silent "carriers" of a disease mutation. The disease only appears in a child who inherits two defective copies of a particular gene from two parents who are carriers. Diseases and other traits inherited in this manner are referred to as Mendelian. Thousands of Mendelian diseases of metabolism and other physiological functions have been described in the medical literature.

Although each individual Mendelian disease mutation is relatively rare, they are cumulatively so common that nearly every human being is a carrier for at least one. Carrier testing can identify two potential parents who have the same mutation and thus have a 25% likelihood of transmitting the corresponding disease to their child.

The vast majority of heritable attributes that distinguish one person from another in morphology, physiology, disease resistance and susceptibility, and mental function result from complex interactions among multiple genes and non-gene loci. Therefore, in most cases, the likelihood that two healthy parents will have a child with genetically-influenced health problems cannot be determined by simply comparing the carrier status of each individual since carrier status has no meaning in the context of a complex genetic trait.

Over the last decade, a pair of conceptual and technological breakthroughs has revolutionized the practice and potential of human genetic analysis. The conceptual breakthrough emerged from the discovery that most genetic variations in the global human population are confined to a limited number of chromosomal positions where one of two letters in the DNA alphabet can occur. These variant genomic positions are called single nucleotide polymorphism ("SNP") loci.

The SNP conceptual breakthrough alone would not have been enough to transform human genetics if the process of determining DNA genotypes remained as tedious as it had been just a few years earlier. But high complexity DNA microarrays allowed the development of a technology for cheaply screening increasingly large numbers of SNPs or CNPs at ever-lower costs. A current state-of-the-art DNA microarray can assay over two million genotypes in an individual human genome.

Advances in DNA microarray design have enabled the detection of many types of characterized genetic variants. Whether simple or complex, most types of genetic variants can be defined in molecular terms as unique SNPs or CNPs for the purpose of analysis.

The ultimate description of a genome is its two 3 billion base pair long DNA sequences. The cost of obtaining a complete personal genome sequence is dropping rapidly. Scientists predict that it will become affordable to average consumers within a few years.

High complexity DNA microarray technologies, high throughput whole genome sequencing, and accompanying information technologies have revolutionized the field of human genetics, with extraordinary advances in understanding the genetic basis for complex traits and an enormous depth of public-access genetic datasets that increase in size daily.

Among other recent advances, scientists can now use cost-effective tools to analyze a patient's genome and predict susceptibility to thousands of medical conditions, including mental illness, neurological diseases, cancer, stroke and heart disease.

While progress has been made in developing computational tools that use information from an individual's genome to predict the likelihood of disease for that person, these tools cannot be applied to the pre-conception prediction of disease in a person's child. Thus, there is a need for methods of assessing the inheritance of such complex attributes prior to, or in place of, conception.

SUMMARY OF THE INVENTION

A pre-conception method is provided herein for predicting the likelihood that a hypothetical child of any two persons, of opposite or same sex, who may or may not be fertile, will express any trait or disease that is subject to genetic influences that have been previously characterized, completely or partially.

Based on an application of formal rules of genetics to a pair of personal genome profile or whole genome sequences, the methods allow for the simulation of the generation of multiple VirtualGametes, each of which contains a single allele from each genotype in combinatorial frequencies estimated for naturally produced sperm and eggs.

The simplest form of VirtualGamete production uses Mendel's Law of independent assortment with a random number generator to choose one copy of each genetic locus independently of others for incorporation into a haploid genome profile. Accuracy and resolution is augmented with high complexity personal genome profiles that can be used to provide phasing information and further genotype imputation.

A uniquely derived VirtualGamete from one personal genome is combined with a uniquely derived VirtualGamete from the second personal genome to produce a discrete Virtual Progeny ("VP") genome sampling containing two definitive copies of each locus. This computational process is repeated a sufficient number of times to obtain a reproducible Virtual Progeny genome.

A Virtual Progeny genome is a sufficiently large sampling of discrete genomes that are cumulatively representative of the likelihoods of alternative genotype combinations in a hypothetical child conceived from the two progenitors.

Each discrete sampling that makes up a Virtual Progeny genome is evaluated independently for the likelihood of expressing any trait for which a genetic correlation has been previously determined. The traits associated with each Virtual Progeny sampling are normalized and combined to obtain a Virtual Progeny phenome distribution.

Virtual Progeny may be evaluated for several thousand rare Mendelian diseases as well as hundreds of more common complex diseases such as diabetes, arteriosclerosis, autism, and schizophrenia. Disease likelihood values for a Virtual Progeny sampling can be calculated indirectly by protein modeling, computational analysis, and geographical origin of chromosomal regions, in addition to direct empirical associations.

Evaluation of Virtual Progeny will be informed by additional factors not used on actual individuals, including the likelihood and length of particular chromosome regions that could be inherited in an identical, homozygous form from two heterozygous parents, which correlates with an increased frequency of fetal loss and children born with "birth defects."

Individuals and couples using a third party to reproduce can compare virtual Progeny produced with each potential genetic partner in a database.

Sperm donor and egg donor agencies can use Virtual Progeny to screen out specific client/donor "pairings" that could give rise to offspring with increased disease risk. Sperm donors who represent a heightened genetic risk in specific combination with a particular client will be removed from that client's pool of potential donors. It is likely that these same donors will show no evidence of risk in combination with most other clients. Since the generation of Virtual Progeny does not depend on interpreting genome profiles of the progenitors, it does not involve carrier screening, and is not burdened with problems of false stigmatization.

Same-sex and infertile couples will be able to simulate the genomic profile of their "own" purely hypothetical child and match this profile to the ones created virtually with selected donors.

Individuals searching for a reproductive partner through a matchmaking agency can use Virtual Progeny comparisons to distinguish strong genetic matches based on desired and undesired offspring traits.

Committed couples can use their virtual child's profile to prevent serious conditions through IVF technology or to prepare for their child's unique gifts and needs.

BRIEF DESCRIPTION OF THE DRAWINGS

The foregoing and other objects of the methods disclosed herein, the various features thereof, as well as the methods and compositions themselves, may be more fully understood from the following description, when read together with the accompanying drawings, in which:

FIG. 1B is a schematic illustration showing genome scans expanded into genome profiles with additional imputed genotypes and phasing information for genetic loci 01 through N.

FIG. 1D is a schematic illustration showing a random VirtualGamete from each of Jane Doe and John Smith, the VirtualGametes being combined to form a Virtual Progeny genome sampling.

FIG. 4 is a summary of Virtual Progeny determinations from four matings of a client ("SRS") mated to four potential partners in which each SNP locus has two alleles designated, A and D. Six classes of genotype results are possible for each SNPs or CNPs in a Virtual Progeny genome. The number of SNPs or CNPs in each class is shown in each mating.

FIGS. 5A-5F are a schematic representation showing various diseases or traits associated with various SNPs or CNPs together with the genotype results of simulated mating of one woman subject to four potential partners.

FIGS. 6A and 6B are a graphical representation of 100 haplopaths (H1-H100) across 9 SNP loci numbered 64-72, generated from 100 Monte Carlo simulations, where homologue index numbers are (0,1).

DETAILED DESCRIPTION

Figure 1A:
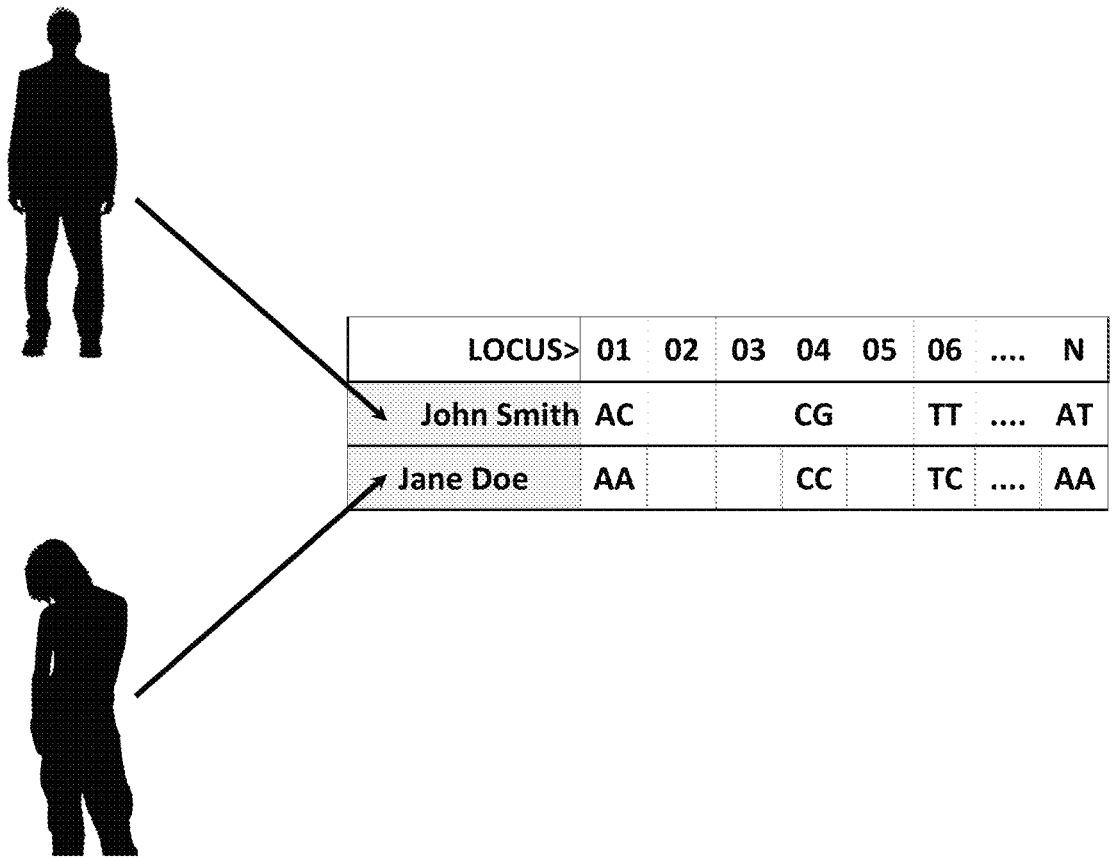
FIG. 1A is a schematic illustration of an exemplary protocol for creating Virtual Progeny where DNA samples from two individuals (Jane Doe and John Smith) are processed to generate genome scans.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "about" is used herein to mean a value − or +20% of a given numerical value. Thus, "about 60%" means a value of between 60−(20% of 60) and 60+(20% of 60) (i.e., between 48 and 70).

As used herein, "haploid cell" refers to a cell with a haploid number (n) of chromosomes.

"Gametes", as used herein, are specialized haploid cells (e.g., spermatozoa and oocytes) produced through the process of meiosis and involved in sexual reproduction.

As used herein, "gametotype" refers to single copies with one allele of each of one or more loci in the haploid genome of a single gamete.

As used herein, an "autosome" is any chromosome exclusive of the X and Y sex chromosomes.

As used herein, "diploid cell" has a homologous pair of each of its autosomal chromosomes, and has two copies (2n) of each autosomal genetic locus.

The term "chromosome", as used herein, refers to a molecule of DNA with a sequence of basepairs that corresponds closely to a defined chromosome reference sequence of the organism in question.

The term "gene", as used herein, refers to a DNA sequence in a chromosome that codes for a product (either RNA or its translation product, a polypeptide) or otherwise plays a role in the expression of said product. A gene contains a DNA sequence with biological function. The biological function may be contained within the structure of the RNA product or a coding region for a polypeptide. The coding region includes a plurality of coding segments ("exons") and intervening non-coding sequences ("introns") between individual coding segments and non-coding regions preceding and following the first and last coding regions respectively.

As used herein, "locus" refers to any segment of DNA sequence defined by chromosomal coordinates in a reference genome known to the art, irrespective of biological function. A DNA locus can contain multiple genes or no genes; it can be a single base pair or millions of base pairs.

As used herein, a "polymorphic locus" is a genomic locus at which two or more alleles have been identified.

As used herein, an "allele" is one of two or more existing genetic variants of a specific polymorphic genomic locus.

As used herein, a "single nucleotide polymorphism" or "SNP" is a particular base position in the genome where alternative bases are known to distinguish one individual from another. Most categories of more complex genetic variants can be reduced for analytical purposes to one or a few defining SNPs or CNPs.

As used herein, a "copy number variant" or "CNV" is a deletion or duplication of a large block of genetic material that exists in a population at a frequency less than 1%.

As used herein, a "copy number polymorphism" or "CNP" is a deletion or duplication of a large block of genetic material that exists in a population at a frequency of greater than 1%. Since a CNV in one population can be a CNP in a second population, the two terms can be used interchangeably As used herein, "genotype" refers to the diploid combination of alleles at a given genetic locus, or set of related loci, in a given cell or organism. A homozygous subject carries two copies of the same allele and a heterozygous subject carries two distinct alleles. In the simplest case of a locus with two alleles "A" and "a", three genotypes can be formed: A/A, A/a, and a/a.

As used herein, "genotyping" refers to any experimental, computational, or observational protocol for distinguishing an individual's genotype at one or more well-defined loci.

As used herein, a "haplotype" is a unique set of alleles at separate loci that are normally grouped closely together on the same DNA molecule, and are observed to be inherited as a group. A haplotype can be defined by a set of specific alleles at each defined polymorphic locus within a haploblock.

As used herein, a "haploblock" refers to a genomic region that maintains genetic integrity over multiple generations and is recognized by linkage disequilibrium within a population. Haploblocks are defined empirically for a given population of individuals.

As used herein, "linkage disequilibrium" is the non-random association of alleles at two or more loci within a particular population. Linkage disequilibrium is measured as a departure from the null hypothesis of linkage equilibrium, where each allele at one locus associates randomly with each allele at a second locus in a population of individual genomes.

As used herein, a "genome" is the total genetic information carried by an individual organism or cell, represented by the complete DNA sequences of its chromosomes.

As used herein, a "genome profile" is a representative subset of the total information contained within a genome. A genome profile contains genotypes at a particular set of polymorphic loci.

As used herein, a "personal genome profile", abbreviated PGP, is the genome profile of a particular individual person.

As used herein, a genetic "trait" is a distinguishing attribute of an individual, whose expression is fully or partially influenced by an individual's genetic constitution.

As used herein, a "phenotype" is a class of alternative traits which may be discrete or continuous.

As used herein, a "haplopath" is a haploid path laid out along a defined region of a diploid genome by a single iteration of a Monte Carlo simulation or a single chain generated through a Markov process. A haplopath can be formed by starting at one end of a personal chromosome or genome and walking from locus to locus, choosing a single allele at each step based on available linkage disequilibrium information, inter-locus allele association coefficients, and formal rules of genetics that describe the natural process of gamete production in a sexually reproducing organism. A "haplopath" is generated through the application of formal rules of genetics that describe the reduction of the diploid genome into haploid genomes through the natural process of meiosis.

As used herein, a "Virtual Gamete" is a single haplopath that extends across an entire genome.

As used herein, a "Virtual Progeny genome sampling" is the discrete genetic product of two Virtual Gametes.

As used herein, a "Virtual Progeny genome" is a collection of discrete Virtual Progeny genome samplings, each generated by combining two uniquely-derived random Virtual Gametes. In some instances, a Virtual Progeny genome is represented as a probability mass function over a sample space of all discrete genome states. In some instances, a Virtual Progeny is an informed simulation of a child or children that might result as a consequence of sexual reproduction between two individuals.

As used herein, a "Virtual Progeny phenome" is a multi-dimensional likelihood function representing the likelihood and/or likely degree of expression of a set of one or more traits from a complete Virtual Progeny genome. In some instances, a Virtual Progeny phenome is represented as a probability mass function over a sample space of discrete or continuous phenotypic states. In some instances, a Virtual Progeny phenome is an informed simulation of a child or children that might result as a consequence of sexual reproduction between two individuals.

As used herein, "partner" includes a marriage partner, sexual or reproductive partner, domestic partner, opposite-sex partner, and same-sex partner.

The methods and compositions disclosed herein relate to assessing the genotypes of individuals and the phenotypes associated with particular genotypes of potential progeny from such individuals. Generally, genome profiles from two individuals are used to determine the probabilities that potential progeny from such individuals will express certain traits, such as an increased risk of disease. Such methods are referred to herein as "Virtual Progeny assessment."

Virtual Progeny Assessment

Disclosed herein are methods of generating a library of potential haploid gamete genomes from an individual diploid subject. The methods comprise obtaining a genomic DNA sample from a diploid subject. In addition, the presence or absence of one or more nucleotide variants (e.g., SNPs or CNPs) are identified at one or more loci of at least one pair of chromosomes of the genomic DNA. In particular embodiments, a haploid gamete genome from a sampling of the potential gamete pool is generated from the diploid genome profile. In such instances, a sampling of a potential very large number of gametes is performed rather than identifying each gamete from a population (i.e., "pool") of gametes. These identified nucleotide variants are compared to a plurality of predetermined genomic sequences of haplotypes having predetermined frequencies at predetermined loci to identify haplotypes present in the genomic DNA.

In certain embodiments, the methods also entail the construction of a diploid genome profile for the subject. In certain embodiments, the genome profile comprises the identified haplotypes and a linkage probability determined by the frequencies of the haplotypes in the plurality of predetermined genomic sequences. A haploid gamete genome for each potential gamete can be generated from the diploid genome profile by generating a combination of the identified haplotypes using the linkage probability for each combination of the identified haplotypes.

Aspects of the methods and systems disclosed herein involve generating a library of potential haploid gamete genomes from an individual diploid subject. The methods comprise providing a database having a plurality of predetermined genomic sequences. In certain embodiments, a first proportion of the genomic sequences comprises a first predetermined haplotype adjacent to a second predetermined haplotype. Also, a second proportion of the genomic sequences comprises the first predetermined haplotype adjacent to a third predetermined haplotype. In particular embodiments, genomic DNA sample from the subject is obtained and the presence or absence of one or more nucleotide variants at one or more loci of at least one pair of chromosomes of the genomic DNA is identified. The identified nucleotide variants are compared to the database to allow for identification of a plurality of sample haplotypes present in the at least one pair of chromosomes. In certain embodiments, the plurality of sample haplotypes comprises the first haplotype adjacent to a wobble haplotype. In some embodiments, the wobble haplotype is either the second haplotype or the third haplotype.

The methods further entail a diploid genome profile that is constructed for the at least one pair of chromosomes of the subject from the identified sample haplotypes. The genome profile comprises the first haplotype, the wobble haplotype, and a linkage probability determined by the proportion of the predetermined genomic sequences. The genomic sequences comprise the first haplotype adjacent to the wobble haplotype. A haploid gamete genome is generated for each potential gamete from the diploid genome profile by linearly combining the first haplotype and the wobble haplotype using the linkage probability. The diploid profiles generated from the methods disclosed herein, in some embodiments, comprise additional identified and additional linkage probabilities determined by the proportion of the predetermined genomic sequences that comprise the first predetermined haplotype adjacent to each additional haplotype.

Furthermore, a method of selecting a potential sperm or oocyte donor is further disclosed. Specifically, the donor genomic DNA samples from potential sperm donors or potential oocyte donors are obtained as well as a recipient genomic DNA sample from a potential recipient. The DNA is analyzed to identify the presence or absence of one or more nucleotide variants at one or more loci of at least one pair of chromosomes of the donor genomic DNA samples and the recipient genomic DNA sample. The identified nucleotide variants are compared to a plurality of predetermined genomic sequences of haplotypes having predetermined frequencies at predetermined loci to identify haplotypes present in the donor genomic DNA samples and the recipient genomic DNA sample.

Using this information, a donor diploid genome profile is constructed for each potential donor. Each donor diploid genome profile comprises the identified haplotypes in each donor genomic DNA sample and a linkage probability determined by the frequencies of the identified haplotypes in the plurality of predetermined genomic sequences. In addition, a recipient diploid genome profile for the potential recipient is constructed. As for the donor, the recipient genome profile comprises the identified haplotypes (in this case, the haplotypes in the recipient genomic DNA sample) and a linkage probability determined by the frequencies of the identified haplotypes in the plurality of predetermined genomic sequences. Libraries are generated for donors and recipients, each library comprising potential haploid gamete genomes from a diploid genome profile. Each potential haploid gamete genome is generated by combining the haplotypes identified in the respective genomic DNA samples using the linkage probability for each combination of the identified haplotypes. Each haploid gamete genome is independently combined from each donor library with a second haploid gamete genome from the recipient library to form a library of diploid progeny genomes for each potential donor. The diploid progeny genomes are compared to a database of disease-associated genomes to assess the risk of disease of each potential progeny, wherein a sperm donor or an oocyte donor is eliminated from consideration if an increased risk of disease of the potential progeny is determined.

FIGS. 1A-1F depict an exemplary method of the methods disclosed herein. The exemplary methods shows how to create a Virtual Progeny. As illustrated in FIG. 1A-1F, DNA samples from two individuals are obtained. The samples are then processed by performing genome scans to identify genotypes at genetic markers, such as SNPs or CNPs, present in each individual's genomic DNA. Identified genotypes can be used to expand a personal genome profile by imputation of genotypes at non-processed genetic markers and to determine haplotypes present within each individual's genomic DNA. The likelihoods of association of sequential haplotypes are retrieved from lookup tables generated by the international HapMap project.

Using the identified haplotypes together with association data, a Monte Carlo simulation is performed to generate haplopaths that extend across each genome, resulting in a Virtual Gamete population for each individual. Virtual Gamete from each individual is combined to produce Virtual Progeny genome sampling, each of which is evaluated for corresponding trait likelihood values. The entire process is repeated a large number of times, each time starting with a new Monte Carlo simulation of Virtual Gametes. An integrated Virtual Progeny phenome likelihood distribution is determined to assess the probability that potential progeny express certain traits, such as increased risk of disease.

Genome Scans

As disclosed herein, the methods comprise obtaining a genomic DNA sample from the subject. These methods of assessing potential Virtual Progeny involves performing genome scans on individuals. In certain embodiments, the individuals share a common ancestry. Genome scans can be performed using any of a number of known procedures. For example, a biologic sample from an individual can first be obtained. Such biological samples include, but are not limited to, a bodily fluid (such as urine, saliva, plasma, or serum) or a tissue sample (such as a buccal tissue sample or buccal cell). The biologic sample can then be used to perform a genome scan using known methods. For example, DNA arrays can be used to analyze at least a portion of the genomic sequence of the individual. Exemplary DNA arrays include GeneChip Arrays, GenFlex Tag arrays, and Genome-Wide Human SNP Array 6.0 (available from Affymetrix, Santa Clara, Calif.).

In certain embodiments, whole or partial genome sequence information is used to perform the genome scans. Such sequences can be determined using standard sequencing methods including chain-termination (Sanger dideoxynucleotide), dye-terminator sequencing, and SOLiD$^{T*}$ sequencing (Applied Biosystems). Whole genome sequences can be cut by restriction enzymes or sheared (mechanically) into shorter fragments for sequencing. DNA sequences can also be amplified using known methods such as PCR and vector-based cloning methods (e.g., *Escherichia coli*).

In some embodiments, at least a portion of an individual's genetic material (e.g., DNA, RNA, mRNA, cDNA, other nucleotide bases or derivative thereof) is scanned or sequenced using, e.g., conventional DNA sequencers or chip-based technologies, to identify the presence or absence of one or more SNPs or copy number polymorphisms ("CNPs") and their corresponding alleles.

A scanning step can involve scanning at least about 1,000 bases, at least about 5,000 bases, at least about 10,000 bases, at least about 20,000 bases, at least about 50,000 bases, at least about 100,000 bases, at least about 200,000 bases, at least about 500,000 bases, at least about 1,000,000 bases, at least about 2,000,000 bases, at least about 5,000,000 bases, at least about 10,000,000 bases, at least about 20,000,000 bases, at least about 50,000,000 bases, at least about 100,000,000 bases, at least about 200,000,000 bases, at least about 500,000,000 bases, at least about 1,000,000,000 bases, at least about 2,000,000,000 bases, or at least 3,000,000,000 bases of an individual's genetic material.

In certain instances, nucleotide bases are scanned from a first set of individuals (e.g., at least about 10 individuals, at least about 20 individuals, at least about 30 individuals, at least about 40 individuals, at least about 50 individuals, at least about 100 individuals, at least about 250 individuals, at least about 500 individuals, or more), and genetic variations between individuals are identified. Genetic variation data generated from each individual can be compared with genetic variation data generated from other individuals in a first set of individuals to discover genetic variations among the first group of individuals.

The variations identified in the first set of individuals can be used in subsequent studies in which such variations are analyzed to determine if they are associated with a phenotype-of-interest. These variations can include, e.g., SNPs or CNPs, common SNPs or CNPs, informative SNPs or CNPs, rare SNPs or CNPs, deletions, insertions, or frameshift mutations. Such genetic variations can be detected in, e.g., genomic DNA, RNA, mRNA, or derivatives thereof. In some instances, genetic variations scanned and/or identified are informative SNPs or CNPs.

In certain instances, instead of scanning and reading all of the bases from each genome or all common SNPs or CNPs, a limited number of informative SNPs or CNPs, e.g., about 300 to about 500,000, can be scanned or read. Thus, while in some instances scanning whole genomes is contemplated, in other instances, only specific chromosomes, loci, common SNPs or CNPs, or informative SNPs or CNPs are scanned and/or used. Specific chromosomes, loci, common SNPs or CNPs, or informative SNPs or CNPs can be selected based on prior knowledge that such regions are related to a particular phenotype of interest.

In some instances, the scanning step is supplemented and/or substituted by obtaining data on genetic variations from databases. These genomic sequences have been predetermined. Such databases can provide, for example, a list of identified genetic variations (e.g., SNPs or CNPs or haplotypes) or genotyping data on particular individuals or populations. Examples of publicly available databases useful in the methods described herein include, but are not limited to, UCSC's Genome Browser, NCBI's dbSNP, MIT's human SNP database, University of Geneva's human Chromosome 21 SNP database, and the University of Tokyo's SNP database. Other databases known in the art can be used in conjunction with the methods described herein.

Because of the haplotype structure of the human genome, analysis of a relatively small number of SNP loci can be used to profile an entire human genome. For example, a haplotype, containing dozens or hundreds of SNP alleles, can be "tagged" with just a few well-chosen "Tag SNPs or CNPs". A nearly complete whole genome profile of an individual can thus be obtained, e.g., by using a DNA microarray that distinguishes genotypes at around 500,000 Tag SNPs or CNPs.

The methods disclosed herein are described below and are illustrated by haploblock information obtained from the International HapMap project (hapmap.org) for a population of European ancestry. In the exemplary method, the presence or absence of one or more nucleotide variants (e.g., SNPs or CNPs) are identified at one or more loci of at least one pair of chromosomes of the genomic DNA and these identified nucleotide variants are compared to a plurality of predetermined genomic sequences of haplotypes having predetermined frequencies at predetermined loci to identify haplotypes present in the genomic DNA. In addition, a haplogroup and its haplotype members can be represented in tabular form for a 14,699 base region of human chromosome 15 from position 25,942,585 to 25,957,284 in the hg18 build of the human reference genome, which is given an index number of "x=69" for this particular download. This haplogroup contains X, =18 loci with unique IDs displayed in row 0, and v=6 haplotype variants represented in rows 1-6. The European frequency of each haplotype is indicated in the first column. The six shown add up to 96% of total variation. The block of elements with bolded perimeter represents a modified stochastic matrix ("A$^x$") with the observed joint frequencies of occurrence of the corresponding row haplotype of X together with row haplotype k of haplogroup X+1. The "L" term in the following equations is " . . . " Furthermore, the first "a" term in the following equation is →.

$$A^x = [l^X_{i,\lambda+k}]a[a^X_{i,k}]_{i=1,L,v_X;k=1,v_{X+1}}$$

For convenience in describing the genetic algorithms presented in this embodiment, the same tabular format shown in Table 1 below and the same formal genetic notation described below is used to denote all loci and meta-loci with one or more loci, whether variant or non-variant. Note that the tables below show haplotypes and association matrices.

TABLE 1

(Table 1 discloses SEQ ID Nos: 1-6, respectively, in order of appearance.)

| X = 69 | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|
| | 69 | | | | | | | | | | | | | | | | | | | 1 | 2 | 3 | 4 |
| 1 | 0.425 | C | A | C | G | C | G | T | G | C | G | G | T | G | C | G | G | G | C | 0.425 | 0.000 | 0.000 | 0.000 |
| 2 | 0.267 | C | A | A | G | C | G | T | G | C | G | A | T | G | C | G | G | G | C | 0.267 | 0.000 | 0.000 | 0.000 |
| 3 | 0.117 | C | A | C | G | C | G | T | G | C | G | G | T | A | C | G | G | G | C | 0.117 | 0.000 | 0.000 | 0.000 |
| 4 | 0.067 | A | C | C | A | T | A | T | G | T | G | G | C | G | T | A | T | A | T | 0.000 | 0.067 | 0.000 | 0.000 |
| 5 | 0.058 | C | C | C | G | C | G | T | G | C | G | G | T | G | T | G | G | G | C | 0.000 | 0.000 | 0.058 | 0.000 |
| 6 | 0.025 | A | C | C | G | C | G | C | A | C | T | G | T | G | T | G | T | G | C | 0.000 | 0.000 | 0.000 | 0.025 |
| var: 6 | | 96% of the population | | | | | chr 15 from 25,942,585 to 25,957,284 = 14,699 bases | | | | | | | | | | | | | | | | |
| G#1: | AM | CC | | | CC | | | | | | GG | AG | | GG | | | GG | GG | CC | (1,2) | | | |
| G#2: | LMS | | AC | CC | AG | CT | | | | | GG | GG | | AG | | | GT | AG | CT | (3,4) | | | |

$L^X$ := indexed meta-locus; X := meta-locus index number a $[l_{00}]$ $\lambda$ := number of loci; locus $\langle j \rangle$ data a $[l^X_{*j}]$; $j \in (1, L, \lambda)$;

$v$ := number of variants or haplotypes; variant $\langle i \rangle$ a $[l^X_{i*}]$: $i \in (1, L, v)$ $f(i)$ := population frequency of variant $\langle i \rangle$ a $[l^X_{i0}]$ $f(\langle i \rangle^X | \langle k \rangle^{X+1})$ a $[l^X_{i,\lambda+k}] \equiv [a^X_{i,k}]$ In the preceding equation, all "L" terms with the exception of the first term represents " . . . " In addition, the "a" terms represent n is →. As shown above, genome scans performed for two individuals ("AM" and "LMS") identify the presence of particular bases at loci 1, 5, 10, 11, 13, and 16-18 for "AM," and particular bases as loci 2-6, 10, 11, 13, and 16-18 for "LMS."

Representations of Genomes and Genotype Phasing

The methods further comprise comparing the plurality of predetermined genomic sequences of haplotypes having predetermined frequencies at predetermined loci to identify haplotypes present in the genomic DNA. In certain embodiments, the assessment of Virtual Progeny includes imputing from publicly available information to further characterize the genotypes of individuals. For example, through an automated process, the composition of haplogroup 69 described above can be reduced to haplotypes 1 and 2 for the "AM" genome, and haplotypes 3 and 4 for "LMS" (Table 2). With the assignment of haplotypes, additional association information can be obtained from the public database for a personal genome as shown in the Tables 3 and 4.

A useful, simplified formulation of the extended genotype (g) carried by an individual person (W) at a previously defined haplogroup (X) takes the form of the following 3×3 matrix containing a 2×2 stochastic matrix partition derived from the haplogroup lookup table, where each element contains the empirically-determined joint frequency of haplotypes $\langle i \rangle^X_i$ with $\langle \kappa \rangle^{X+1}_j$.

$$g_x(W) = \begin{bmatrix} X & \langle \kappa \rangle^{X+1}_1 & \langle \kappa \rangle^{X+1}_2 \\ \langle i \rangle^X_1 & a_{\langle i \rangle^X_1, \langle \kappa \rangle^{X+1}_1} & a_{\langle i \rangle^X_1, \langle \kappa \rangle^{X+1}_2} \\ \langle i \rangle^X_2 & a_{\langle i \rangle^X_2, \langle \kappa \rangle^{X+1}_1} & a_{\langle i \rangle^X_2, \langle \kappa \rangle^{X+1}_2} \end{bmatrix},$$

$\langle i \rangle^X \in (1, L, v_X)$, $\langle \kappa \rangle^{X+1} \in (1, L, v_{X+1})$ From the data shown above for "LMS" and "AM", the following prenormalization genotype matrices can be obtained (Tables 3 and 4).

TABLE 2

(Table 2 discloses SEQ ID Nos: 1-4, respectively, in order of appearance.)

| X = 69 | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|
| | 18 loci | | | | | | | | | | | | | | | | | | | 1 | 2 | 3 | 4 |
| G#1: | AM | CC | | | CC | | | | | | GG | AG | | GG | | | GG | GG | CC | | | | |
| 1 | 0.425 | C | A | C | G | C | G | T | G | C | G | G | T | G | C | G | G | G | C | 0.425 | 0.000 | 0.000 | 0.000 |
| 2 | 0.267 | C | A | A | G | C | G | T | G | C | G | A | T | G | C | G | G | G | C | 0.267 | 0.000 | 0.000 | 0.000 |
| G#2: | LMS | | AC | CC | AG | CT | | | | | GG | GG | | AG | | | GT | AG | CT | | | | |
| 3 | 0.117 | C | A | C | G | C | G | T | G | C | G | G | T | A | C | G | G | G | C | 0.117 | 0.000 | 0.000 | 0.000 |
| 4 | 0.067 | A | C | C | A | T | A | T | G | T | G | G | C | G | T | A | T | A | T | 0.000 | 0.067 | 0.000 | 0.000 | chr 15 from 25,942,585 to 25,957,284 = 14,699 bases

TABLE 3

|  | 69 | 1 | 1 |
|---|---|---|---|
| $g_{69}$ (AM) = | 1 | 0.425 | 0.425 |
|  | 2 | 0.267 | 0.267 |

TABLE 4

|  | 69 | 1 | 2 |
|---|---|---|---|
| $g_{69}$ (LMS) = | 3 | 0.117 | 0.000 |
|  | 4 | 0.000 | 0.067 |

These data represent relationships of adjacent loci in a population, not an individual diploid genome. Thus, in certain embodiments, initial association matrices can be parsed with diploid genome consistency rules, leading to a transformation of:

$$\left[ a_{(i)_i^X, (k)_j^{X+1}} \right].$$

Associations can be determined according to several criteria including, e.g., population data and inter-locus distance on a chromosome. When no association information is available for sequential loci, independent assortment can be assumed:

$$[a_{i,k}^X]_{i=1,2;\ k=1,2} = 0.5$$

The complete formulation of a whole genome profile can be an indexed set of genotype matrices:

$$G(W) = \{g_X(W) : X=1, \ldots, N\}$$

An example of a portion of two whole genome profiles across a distance of 110,000 bases of chromosome 11 for personal genome scans for "AM" and "LMS" that was expanded directly (through a haplogroup lookup table into phased genetic information at over 400 individual SNP loci) is given below (Table 5).

Formation of Virtual Gametes Using Haplopaths

In particular embodiments, a haploid gamete genome for each potential gamete is generated from the diploid genome profile by generating a combination of the identified haplotypes using the linkage probability for each combination of the identified haplotypes. In some embodiments, the Virtual Gametes are then generated using a computer simulation of gamete production from a diploid parental genome profile. The simulated haplopath can be computed or generated by subjecting the parental genome to formal rules of genetics that operate naturally during meiosis and gamete production.

Formal rules of genetics are known in the art, and are mathematical formulas or algorithms that serve as abstract representations of the biological processes of sexual reproduction. Rules are based on allele segregation, independent assortment, linkage between genetic loci, recombination suppression, Hardy-Weinberg equilibria, and other probabilistic genetic processes. Formal rules can be used to estimate the likelihood of transmission of particular alleles and combinations of alleles at multiple loci, from an individual to a gamete.

The geographic origin of a parental genome, or subregion thereof, can provide population-specific allele and genotype frequency information that can be incorporated into computational models that predict genotypic and phenotypic probabilities of Virtual Progeny.

A Virtual Gamete includes one permutation of a haploid genome path, or haplopath (H), from one end of a computed genome profile (X=1) to the other (X=N). Each haplopath includes a single allele (variant or haplotype) from each meta-locus, defined by the index number of the chromosomal homologue.

A haplopath can be initiated with a random number generator (e.g., such as a Monte Carlo method) that chooses a random allele(i) at a random initializing locus in the set of N such loci. Each prior and subsequent allele along the haplopath can be generated according to normalized likelihoods derived from locus-specific association matrices.

$$Pr(L_k^{X+1}) = \frac{[a_{i,k}^X]}{([a_{i,1}^X] + [a_{i,2}^X])}; \ i, k \in (1, 2)$$

For each Monte Carlo haplopath $[H_{i1}]$ that is generated computationally, a reciprocal haplopath $[H_{i1}]$ can be created

TABLE 5

| 1 | | | 2 | | | 3 | | | 4 | | | 5 | | |
|---|---|---|---|---|---|---|---|---|---|---|---|---|---|---|
| 64 | 1 | 3 | 65 | 1 | 1 | 66 | 1 | 2 | 67 | 1 | 3 | 68 | 1 | 2 |
| 1 | 0.625 | 0.125 | 1 | 0.617 | 0.617 | 1 | 0.492 | 0.283 | 1 | 0.242 | 0.033 | 1 | 0.350 | 0.083 |
| 1 | 0.625 | 0.125 | 3 | 0.125 | 0.125 | 1 | 0.492 | 0.283 | 2 | 0.300 | 0.008 | 3 | 0.075 | 0.008 |
| 64 | 1 | 3 | 65 | 1 | 1 | 66 | 1 | 1 | 67 | 1 | 1 | 68 | 3 | 4 |
| 1 | 0.625 | 0.125 | 1 | 0.617 | 0.617 | 1 | 0.492 | 0.492 | 1 | 0.242 | 0.242 | 1 | 0.117 | 0.025 |
| 1 | 0.625 | 0.125 | 3 | 0.125 | 0.125 | 1 | 0.492 | 0.492 | 1 | 0.242 | 0.242 | 1 | 0.117 | 0.025 |
| 25,861,367 | | | 25,879,159 | | | 25,909,368 | | | 25,938,449 | | | 25,940,622 | | |

| 6 | | | 7 | | | 8 | | | 9 | | |
|---|---|---|---|---|---|---|---|---|---|---|---|
| 69 | 1 | 1 | 70 | 1 | 1 | 71 | 1 | 1 | 72 | 1 | 1 |
| 1 | 0.425 | 0.425 | 1 | 0.825 | 0.825 | 1 | 0.817 | 0.817 | 1 | 0.683 | 0.683 |
| 2 | 0.267 | 0.267 | 1 | 0.825 | 0.825 | 1 | 0.817 | 0.817 | 1 | 0.683 | 0.683 |
| 69 | 1 | 2 | 70 | 1 | 2 | 71 | 1 | 2 | 72 | 3 | 3 |
| 3 | 0.117 | 0.000 | 1 | 0.825 | 0.000 | 1 | 0.817 | 0.008 | 1 | 0.017 | 0.017 |
| 4 | 0.000 | 0.067 | 2 | 0.000 | 0.075 | 2 | 0.000 | 0.075 | 2 | 0.033 | 0.033 |
| 25,942,585 | | | 25,959,712 | | | 25,967,383 | | | 25,971,652 | | | with alleles present on the opposite homologue at every locus. This converse haplopath represents the sister/brother gamete of a simulated haplopath:

$$H_{i1}=\{h_1,h_2,\ldots,h_N\}, h_X \in (1,2)$$

$$H_{i1}=\{h_1,h_2,\ldots,h_N\}, h_X \in (1,2); h_{X,i} \notin (h_{X,i1})$$

The inclusion of converse haplopaths in a Virtual Gamete pool can increase consistency of the simulated data with Mendel's first law of equal segregation at every locus. FIG. 6 shows an example of 100 iterations of a Monte Carlo run on the genomic region shown above, where homologue index numbers have been converted from (1,2) to (0,1).

Formation of Virtual Progeny

In further embodiments, the Virtual Progeny genome is a collection of permutations of diploid genomes that can each be formed by combining a random Virtual Gamete from one parent (the paternal line, pat) with a random Virtual Gamete from a second parent (the maternal line, mat). Each permutation of a Virtual Progeny genome comprises a discrete set of defined integer genotypes. In one embodiment, a single permutation (i) of a Virtual Progeny genome can take the following form:

$$G_i^{VP} = f(G^{pat}, G^{mat})$$

$$= \left\{ \begin{bmatrix} h_X^{pat} \\ h_X^{mat} \end{bmatrix} : X = 1, \ldots, N \right\} \rightarrow \{g_X(i): X = 1, \ldots, N\}$$

In exemplary methods, a Virtual Progeny genome can comprise a set of individual permutations of Virtual Progeny genomes:

$$G^{VP}=\{G_1^{VP}, G_2^{VP}, \ldots\}$$

A phenome can comprise a measure of phenotypes and traits expressed by a diploid organism over the time period of its life. Numerous discrete or continuous phenotypes associated with discrete genotypes are listed on databases maintained at the National Institutes of Health division of Bioinformatic Information and other public databases. Additional sources of discrete or continuous phenotypes associated with discrete genotypes are located in PubMed, the UCSC browser, NCBI (fancy output genomic browser), Online Mendelian Inheritance in Man ("OMIM"), SNPedia, GeneTests, Entrez Gene, HuGENavigator, HuGENavigator/Genopedia/Search, HuGENavigator/Phenopedia/Search, NextBio Database, and Genetic Association Database. In addition, databases for SNP and variant datasets include SNP Cluster Report, Genome-Wide Association Studies (National Human Genome Research Institute), Autism Chromosome Rearrangement Database (hosted by The Centre for Applied Genomics), and the Database of Genomic Variants (hosted by The Centre for Applied Genomics).

The Virtual Progeny phenome ($ph^{VP}$) can comprise a single probability density function defined by the summation of the weighted set of phenomes that are individually associated with each permutation of a Virtual Progeny genome.

In some methods, prior population genetic data can be used to predict the population or populations of origin for a trait-affecting locus, which can be incorporated into models that can be used to predict trait likelihoods of virtual or actual progeny. Phenotypes associated with all genotypes in the Virtual Progeny sample space can be integrated to produce an overall assessment of phenotypic likelihoods (in terms of penetrance and expressivity) for each individual trait, alone or in combination.

The following is an example showing the application of the methods described herein. The actual methods can cover many more genes with a larger number of loci.

The method entails a genotyping panel with the disease impacted by each locus, the official name of the locus, the alleles at each locus that are probed, the frequency of these alleles in the population being analyzed, standard reference names for probes that detect each allele, (an abbreviated name for each allele for the purposes of this illustration), and the impact of the allele on disease risk or disease expression within each genotypic context. Such a description is shown in Table 1, which shows information for a two-locus genotyping panel.

TABLE 6

| Disease | genome locus | allele | freq. | probe | abb. | effect of allele in genotype |
|---|---|---|---|---|---|---|
| Cystic fibrosis | CFTR:c.1408A > G | CFTR:p.469V | 0.50 | rs213950G | G | GG: no effect |
| | | CFTR:p.469M | 0.50 | rs213950A | A | AA: 0.002 risk; GA: 0.05 risk |
| | CFTR:c.1521_1523del3 | CFTR:p.508F | 0.98 | rs332TTT | T | TT,Td: no direct effect, but risk of other CF mutations remains |
| | | CFTR:p.508del | 0.02 | rs332del | d | dd: cystic fibrosis, severe |

The findings on genotype-phenotype associations and population frequencies of alleles, including alleles not determined in this analysis, will be used to create a risk table that covers all possible genotype combinations of alleles in the genotyping panel (Table 7).

TABLE 7

| Disease | 2-locus genotype | Risk of disease in virtual child |
|---|---|---|
| Cystic fibrosis | GG,TT | 1/25,000 |
| | GA,TT | 1/192,000 |
| | AA,TT | 1/3,600,000 |
| | GG,dT | 1/75 |
| | GA,dT | 1/1,500 |
| | AA,dT | 1/30,000 |
| | GG,dd | 1/1 |
| | GA,dd | 1/1 |
| | AA,dd | 1/1 |

Genotype data captured from each individual who is a component of the analysis is assembled (Table 8).

TABLE 8

| Individual | 2-locus genotype |
|---|---|
| Donor B | GA,TT |
| Donor F | AA,dT |
| Client #1 | GA,TT |
| Client #2 | AA,TT |

Next, a Monte Carlo algorithm is applied to each individual genotype profile to generate a pool of "Virtual Gametes" containing single alleles from each locus. A virtual gamete from each designated genetic parent is chosen randomly and combined to produce one permutation of a potential child's genotype profile. The process of virtual gamete choice and combination to produce a diploid genome is iterated a sufficient number of times so that the sum of permutations provides a stable estimate of a child's genome likelihood distribution, as illustrated in columns 1 and 2 of Table 9.

TABLE 9

Pairing: Client #1 × Donor B
Monte Carlo-generated Virtual progeny genotypes

| genotype | Likelihood distribution | CF risk from table |
|---|---|---|
| GG,TT | 0.25 | 1/25,000 |
| GA,TT | 0.50 | 1/192,000 |
| AA,TT | 0.25 | 1/3,600,000 |

Normalized Disease Risk for Composite Virtual Progeny cystic fibrosis 1/79,000

The risk of disease associated with each discrete Virtual Progeny genotype is determined from the previously established risk table (from Table 7 into column 3 of Table 9). Disease risks associated with each genotype are weighted according to their appearance in the set of permutations to assign a normalized disease risk to the particular pairing under analysis (Table 10).

TABLE 10

| Genotypes | | | | DONORS | | | | | |
|---|---|---|---|---|---|---|---|---|---|
| Locus #1 | Locus #2 delF508 | | | | | | | | |
| rs213950 -/- | No testing -/- | RISK 2,500 | | A 24% | B 48% | C 24% | D 1% | E 2% | F 1% |
| | Client | 1 | G/A, F/F X | G/G, F/F | G/A, F/F | A/A, F/F | G/G, del/F | G/A, del/F | A/A, del/F |
| G/G | F/F | 25,000 | | 0.500 | 0.250 | 0.000 | 0.250 | 0.125 | 0.000 |
| G/A | F/F | 191,755 | | 0.500 | 0.500 | 0.500 | 0.250 | 0.250 | 0.250 |
| A/A | F/F | 3,634,742 | | 0.000 | 0.250 | 0.500 | 0.000 | 0.125 | 0.250 |
| G/G | del/F | 75 | | 0.000 | 0.000 | 0.000 | 0.250 | 0.125 | 0.000 |
| G/A | del/F | 1,500 | | 0.000 | 0.000 | 0.000 | 0.250 | 0.250 | 0.250 |
| A/A | del/F | 30,000 | | 0.000 | 0.000 | 0.000 | 0.000 | 0.125 | 0.250 |
| n/n | del/del | 1 | | 0.000 | 0.000 | 0.000 | 0.000 | 0.000 | 0.000 |
| | | | 11,638 | 44,233 | 78,888 | 364,291 | 285 | 542 | 5,670 |
| | Client | 2 | A/A, F/F X | G/G, F/F | G/A, F/F | A/A, F/F | G/G, del/F | G/A, del/F | A/A, del/F |
| G/G | F/F | 25,000 | | 0.00 | 0.00 | 0.00 | 0.00 | 0.00 | 0.00 |
| G/A | F/F | 191,755 | | 1.00 | 0.50 | 0.00 | 0.50 | 0.25 | 0.00 |
| A/A | F/F | 3,634,742 | | 0.00 | 0.50 | 1.00 | 0.00 | 0.25 | 0.50 |
| G/G | del/F | 75 | | 0.00 | 0.00 | 0.00 | 0.00 | 0.00 | 0.00 |
| G/A | del/F | 1,500 | | 0.00 | 0.00 | 0.00 | 0.50 | 0.25 | 0.00 |
| A/A | del/F | 30,000 | | 0.00 | 0.00 | 0.00 | 0.00 | 0.25 | 0.50 |
| n/n | del/del | 1 | | 0.00 | 0.00 | 0.00 | 0.00 | 0.00 | 0.00 |
| | | | 103,198 | 191,755 | 364,291 | 3,634,742 | 2,977 | 5,670 | 59,509 |
| | Client | 3 | G/G, F/FX | G/G, F/F | G/A, F/F | A/A, F/F | G/G, del/F | G/A,del/F | A/A, del/F |
| G/G | F/F | 25,000 | | 1.00 | 0.50 | 0.00 | 0.50 | 0.25 | 0.00 |
| G/A | F/F | 191,755 | | 0.00 | 0.50 | 1.00 | 0.00 | 0.25 | 0.50 |
| A/A | F/F | 3,634,742 | | 0.00 | 0.00 | 0.00 | 0.00 | 0.00 | 0.00 |
| G/G | del/F | 75 | | 0.00 | 0.00 | 0.00 | 0.50 | 0.25 | 0.00 |
| G/A | del/F | 1,500 | | 0.00 | 0.00 | 0.00 | 0.00 | 0.25 | 0.50 |
| A/A | del/F | 30,000 | | 0.00 | 0.00 | 0.00 | 0.00 | 0.00 | 0.00 |
| n/n | del/del | 1 | | 0.00 | 0.00 | 0.00 | 0.00 | 0.00 | 0.00 |
| | | | 6,167 | 25,000 | 44,233 | 191,755 | 150 | 285 | 2,977 |

The final result obtained above is used in conjunction with a chosen risk tolerance cutoff to determine whether the donor should be retained or removed from the client pool. If risk tolerance had been set previously at 1/50,000, the result obtained in this example would lead to no action being taken. Donor B would remain in client #1's pool. However, the other donors would be eliminated as potential parents of offspring. In the case of disease or particular traits, an increased likelihood or risk of such disease would have been determined, thereby rendering certain donors eliminated from the pool of potential donors. In certain instances, the potential parent is a sperm donor. In other instances, the potential parent is an oocyte donor.

Figure 2:
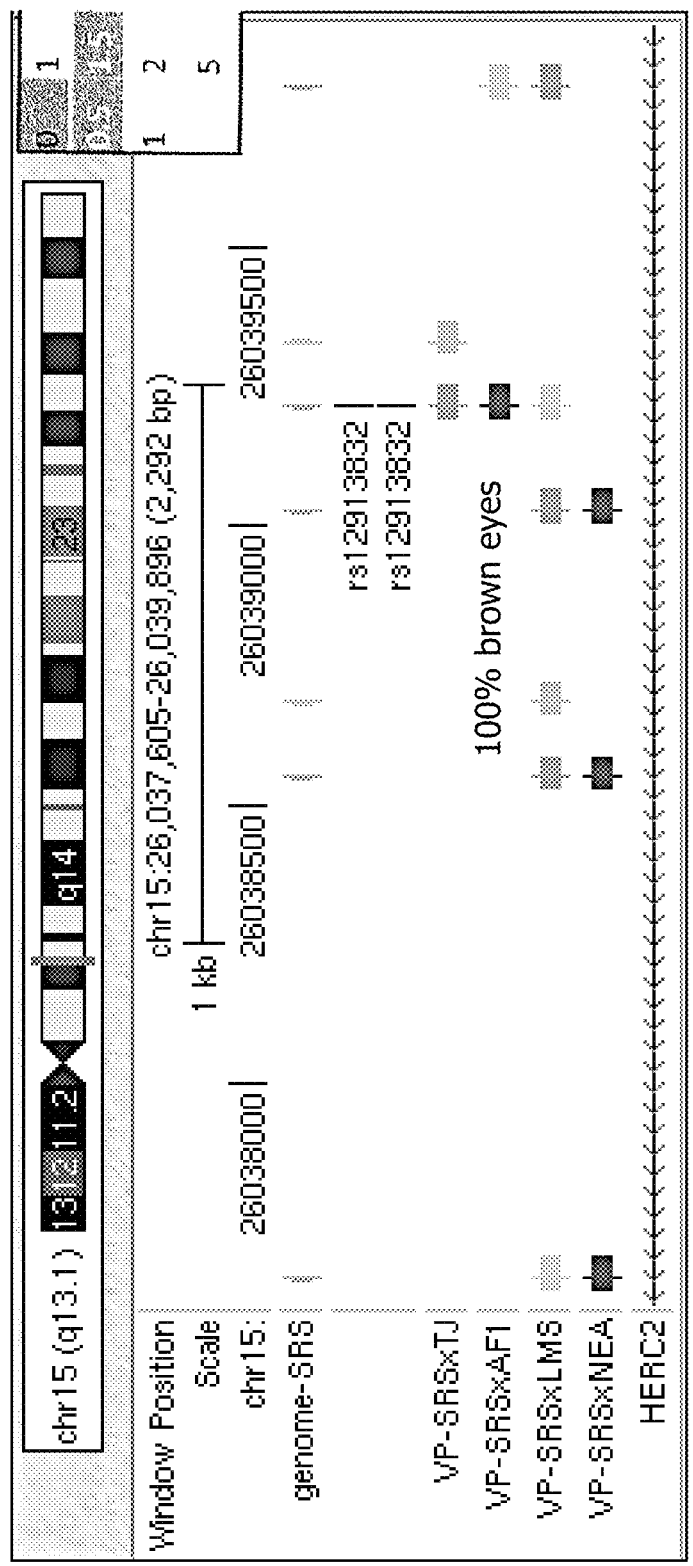
FIG. 2 is a representation of Virtual Progeny results for SRS and four partners in the gene region responsible for blue eye color.

This methodology was used to identify probable phenotypes of Virtual Progeny from the simulated matings of four donors with client SRS (FIG. 2). Virtual Progeny are generated analyzing the potential phenotypes that would be generated from the matings of SRS with four different donors. For VP-SRSxTJ (i.e., a mating of SRS to TJ), the progeny phenotypes will all be blue eyes, while for VP-SRSxAF1 (i.e., a mating SRS to AF1), the phenotypes will all be brown eyes. For VP-SRSxLMS (i.e., a mating SRS to LMS) and VP-SRSxNEA (i.e., a mating SRS to NEA), the Virtual Progeny likelihood phenotype is 50% blue and 50% brown.

TABLE 11

| | | | Categories of donors (in relation to 2-SNP genotype) | | | | | | |
|---|---|---|---|---|---|---|---|---|---|
| Locus #1 rs213950 | Locus #2 delF508 | Clients | | A 24% G/G, F/F | B 48% G/A, F/F | C 24% A/A, F/F | D 1% G/G, del/F | E 2% G/A, del/F | F 1% A/A, del/F |
| –/– | –/– | 2,500 | | | | | | | |
| G/A | F/F | 11,638 | X | 44,233 | 78,888 | 364,291 | 285 | 542 | 5,670 |
| A/A | F/F | 103,198 | X | 191,755 | 364,291 | 3,634,742 | 2,977 | 5,670 | 59,509 |
| G/G | F/F | 6,167 | X | 25,000 | 44,233 | 191,755 | 150 | 285 | 2,977 |

The analysis presented in this illustration can be readily scaled to any number of diseases and loci. The most time-consuming components are genome scans and assessing Virtual Progeny, which only need be performed once. The actual application of the rest of the methodology is entirely automated, and a test run with a panel of 1,000 loci (2,000 probes) was performed in less than one minute on a laptop computer.

Assessing Probability of Trait Expression

In the particular embodiment, the Virtual Progeny genome, which actually comprises a collection of likely genome permutations, or distribution of genome states generated through a Markov process, can be interrogated for associated trait expression. Each discrete genome in the Virtual Progeny collection or distribution can be evaluated independently for expected trait expression, based on published genotype-phenotype associations. The weighted summation of traits expressed by individual genome permutations can yield a Virtual Progeny phenome probability distribution.

The disclosed methods and systems can be used to provide visual representations of differential virtual progeny results for virtual mating of a client with potential donors (FIG. 2). Further, each of the virtual matings are compared. The methods disclosed herein are used to obtain samples, which are processed by performing genome scans to identify SNPs or CNPs present in each individual's genomic DNA. The identified genetic markers are used to expand personal genome data and to determine haplotypes present within each individual's genomic DNA. The likelihoods of association of sequential haplotypes are retrieved from lookup tables generated by the international HapMap project. Using the identified haplotypes together with association data, reiteration of a Monte Carlo simulation is performed to generate a haplopath, resulting in a Virtual Gamete population for each individual. Virtual Gametes from each individual are combined to produce Virtual Progeny genome samplings, each of which is evaluated for corresponding trait likelihood values. Finally, an integrated Virtual Progeny phenome likelihood distribution is determined to assess the probability that potential progeny express certain traits, such as increased risk of disease.

Figure 3:
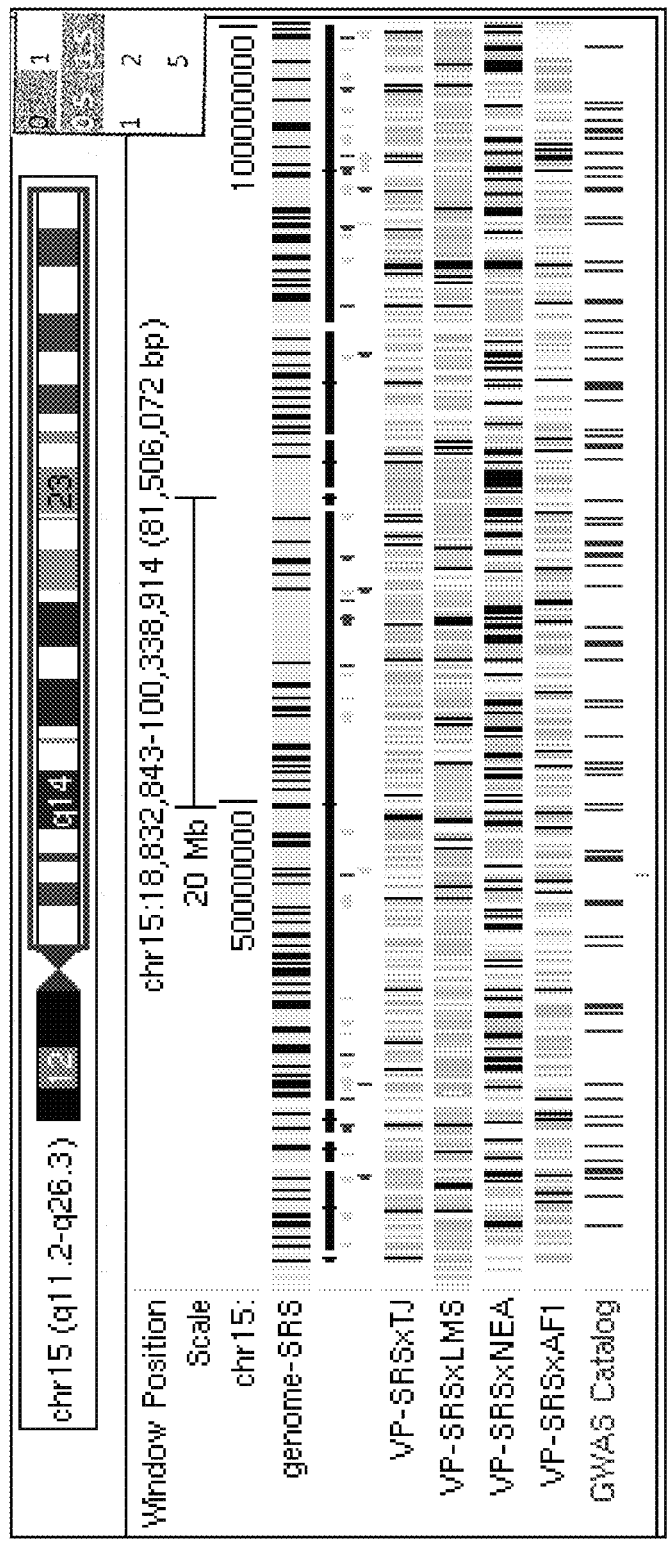
FIG. 3 is a schematic illustration of Virtual Progeny genome profiles containing simulated genotype information at approximately 10,000 SNP loci across 82 million base pairs of chromosome 15. The bottom row shows the location of every SNP locus in this region (each index mark associated with a differential trait).

Such divergence increases radically when more loci are added to the analysis. For example, when 100,000 loci are analyzed, the number of potential genotypes increases to 2100,000 The disclosed methods and systems allow for the analysis of large numbers of loci without the incredible amount of time or uncertainty associated with prior methodologies. FIG. 3 shows an example of a visual representation of Virtual Progeny genome profiles for the matings of the SRS to the four donors, all of which are shown across 82 million base pairs of Chromosome 15. The bottom row shows the loci associated with various traits.

As described above, the probability that Virtual Progeny described herein will have a particular trait can be assessed by comparing discrete Virtual Progeny genome samplings to publicly available databases. FIG. 4 shows an analysis of Virtual Progeny ("VP") genotypes. Each SNP locus has two alleles (A and D), which can produce three distinct genotypes (AA,AD,DD). "A" is used to signify the original "ancestral" allele and "D" is the allele "derived" by mutation. At any one locus, "A" and "D" each refer to empirically determined nucleotide bases A,C,G, or T. Utilizing reference information from databases known in the art and disclosed herein, "A" is used as a reference allele. Using this analytical technique, a SNP genotype is completely described by the number of ancestral alleles it contains (0,1,2). For instance, an integer is used to indicate determination of a single definitive genotype. If a progeny is described using a "0" for a particular allele, then the progeny definitively has zero ancestral alleles at the particular locus. If "1" describes the progeny, the progeny definitively has one ancestral allele at that locus. If "2" describes the progeny, then the progeny definitively has both ancestral alleles. In other words, integers occur when both mates are homozygous for a particular allele. Non-integers (0.5,1.5) indicate restriction to the two genotypes that are ±0.5 removed. In other words, non-integers indicate that one mate was heterozygous for a particular allele. Finally, an out-of-bounds integer (5) is used when data from the two virtual parents is non-informative (i.e., both parents are heterozygous at that locus). In the example provided in FIG. 4, the number of loci falling into the categories 0, 0.5, 1, 1.5, 2, and 5 are shown. As is apparent, each partner provides a different profile for SNPs or CNPs found in the reference databases.

FIG. 5 provides a more detailed view of actual SNPs or CNPs that are known and can be analyzed using the methods and systems disclosed herein. Various SNPs or CNPs and the results of simulated mating of one woman subject to four potential partners is again shown as either an integer (0, 1, or 2), a non-integer (0.5 or 1.5), or as non-informative (5) (FIG. 5). As in FIG. 4, the profile of each VP of each mating is provided for the various traits and diseases. The data comparison identified virtual progeny genotypes at over 1,300 SNP loci that influence over 100 disease traits shown in the table.

Traits

Nonlimiting examples of traits that may assessed using the methods described herein include or relate to ability to roll the tongue, ability to taste PTC, acute inflammation, adaptive immunity, addiction(s), adipose tissue, adrenal gland, age, aggression, amino acid level, amyloidosis, anogenital distance, antigen presenting cells, auditory system, autonomic nervous system, avoidance learning, axial defects or lack thereof, B cell deficiency, B cells, B lymphocytes (e.g., antigen presentation), basophils, bladder size/shape, blinking, blood chemistry, blood circulation, blood glucose level, blood physiology, blood pressure, body mass index, body weight, bone density, bone marrow formation/structure, bone strength, bone/skeletal physiology, breast size/shape, bursae, cancellous bone, cardiac arrest, cardiac muscle contractility, cardiac output, cardiac stroke volume, cardiomyopathy, cardiovascular system/disease, carpal bone, catalepsy, cell abnormalities, cell death, cell differentiation, cell morphology, cell number, cell-mediated immunity, central nervous system, central nervous system physiology, chemotactic factors, chondrodystrophy, chromosomal instability, chronic inflammation, circadian rhythm, circulatory system, cleft chin, clonal anergy, clonal deletion, T and B cell deficiencies, conditioned emotional response, congenital skeletal deformities, contextual conditioning, cortical bone thickness, craniofacial bones, craniofacial defects, crypts of Lieberkuhn, cued conditioning, cytokines, delayed bone ossification, dendritic cells (e.g., antigen presentation), Di George syndrome, digestive function, digestive system, digit dysmorphology, dimples, discrimination learning, drinking behavior, drug abuse, drug response, ear size/shape including ear lobe attachment, eating behavior, ejaculation function, embryogenesis, embryonic death, embryonic growth/weight/body size, emotional affect, enzyme/coenzyme level, eosinophils, epilepsy, epiphysis, esophagus, excretion physiology, extremities, eye blink conditioning, eye color/shape, eye physiology, eyebrows shape, eyelash length, face shape, facial cleft, femur, fertility/fecundity, fibula, finger length/shape, fluid regulation, fontanels, foregut, fragile skeleton, freckles, gall bladder, gametogenesis, gastrointestinal hemorrhage, germ cells (e.g., morphology, depletion), gland dysmorphology, gland function, glucagon level, glucose homeostasis, glucose tolerance, glycogen catabolism, granulocytes, granulocytes (e.g., bactericidal activity, chemotaxis), grip strength, grooming behavior, hair color, hair follicle structure/orientation, hair growth, hair on mid joints, hair texture, handedness, harderian glands, head, hearing function, heart, heart rate, heartbeat (e.g., rate, irregularity), height, hemarthrosis, hemolymphoid system, hepatic system, hitchhiker's thumb, homeostasis, humerus, humoral immune response, hypoplastic axial skeleton, hypothalamus, immune cell, immune system (e.g., hypersensitivity), immune system response/function, immune tolerance, immunodeficiency, inability to urinate, increased sensitivity to gamma-irradiation, inflammatory mediators, inflammatory response, innate immunity, inner ear, innervation, insulin level, insulin resistance, intestinal bleeding, intestine, ion homeostasis, jaw, kidney hemorrhage, kidney stones, kidney/renal system, kyphoscoliosis, kyphosis, lacrimal glands, larynx, learning/memory, leukocyte, ligaments, limb dysmorphology, limb grasping, lipid chemistry, lipid homeostasis, lips size/shape, liver (e.g., development/function), liver/hepatic system, locomotor activity, lordosis, lung, lung development, lymph organ development, macrophages (e.g., antigen presentation), mammary glands, maternal/paternal behavior, mating patterns, meiosis, mental acuity, mental stability, mental state, metabolism of xenobiotics, metaphysis, middle ear, middle ear bone, morbidity and mortality, motor coordination/balance, motor learning, mouth, movement, muscle, muscle contractility, muscle degeneration, muscle development, muscle physiology, muscle regeneration, muscle spasms, muscle twitching, musculature, myelination, myogenesis, nervous system, neurocranium, neuroendocrine glands, neutrophils, NK cells, nociception, nose, nutrients/absorption, object recognition memory, ocular reflex, odor preference, olfactory system, oogenesis, operant or "target response", orbit, osteogenesis, osteogenesis/developmental, osteomyelitis, osteoporosis, outer ear, oxygen consumption, palate, pancreas, paralysis, parathyroid glands, pelvis girdle, penile erection function, perinatal death, peripheral nervous system, phalanxes, pharynx, photosensitivity, piloerection, pinna reflex, pituitary gland, PNS glia, postnatal death, postnatal growth/weight/body size, posture, premature death, preneoplasia, propensity to cross the right arm over the left of vice versa, propensity to cross the right thumb over the left thumb when clasping hands or vice versa, pulmonary circulation, pupillary reflex, radius, reflexes, reproductive condition, reproductive system, resistance to fatty liver development, resistance to hyperlipidemia, respiration (e.g., rate, shallowness), respiratory distress or failure, respiratory mucosa, respiratory muscle, respiratory system, response to infection, response to injury, response to new environment (transfer arousal), ribs, salivary glands, scoliosis, sebaceous glands, secondary bone resorption, seizures, self tolerance, senility, sensory capabilities, sensory system physiology/response, sex, sex glands, shoulder, skin, skin color, skin texture/condition, skull, skull abnormalities, sleep pattern, social intelligence, somatic nervous system, spatial learning, sperm count, sperm motility, spermatogenesis, startle reflex, sternum defect, stomach, suture closure, sweat glands, T cell deficiency, T cells (e.g., count), tarsus, taste response, teeth, temperature regulation, temporal memory, tendons, thyroid glands, tibia, touch/nociception, trachea, tremors, trunk curl, tumor incidence, tumorigenesis, ulna, urinary system, urination pattern, urine chemistry, urogenital condition, urogenital system, vasculature, vasoactive mediators, vertebrae, vesicoureteral reflux, vibrissae, vibrissae reflex, viscerocranium, visual system, weakness, widows peak or lack thereof, etc.

Other nonlimiting traits include cognitive ability (Ruano et al., Am. J. Hum. Genet. 86:113 (2010)); Familial Osteochondritis Dissecans (Stattin et al., Am. J. Hum. Genet. 86:126 (2010)); hearing impairment (Schraders et al., Am. J. Hum. Genet. 86:138 (2010)); mental retardation associated with autism, epilepsy, or macrocephaly (Giannandrea et al., Am. J. Hum. Genet. 86:185 (2010)); muscular dystrophies (Bolduc et al., Am. J. Hum. Genet. 86:213 (2010)); Diamond-Blackfan anemia (Doherty et al., Am. J. Hum. Genet. 86:222 (2010)); osteoporotic fractures (Kung et al., Am. J. Hum. Genet. 86:229 (2010)); familial exudative vitreoretinopathy (Poulter et al., Am. J. Hum. Genet. 86:248 (2010)); skeletal dysplasia, eye, and cardiac abnormalities (Iqbal et al., Am. J. Hum. Genet. 86:254 (2010)); Warsaw breakage syndrome (van der Lilij et al., Am. J. Hum. Genet. 86:262 (2010)); arterial calcification of infancy (Lorenz-Depiereux et al., Am. J. Hum. Genet. 86:267 (2010)); hypophosphatemic rickets (Lorenz-Depiereux et al., Am. J. Hum. Genet. 86:267 (2010); Levy-Litan et al., Am. J. Hum. Genet. 86:273 (2010)); rhabdoid tumor predisposition syndrome (Schneppenheim et al., Am. J. Hum. Genet. 86:279 (2010)); and multiple sclerosis (Jakkula et al., Am. J. Hum. Genet. 86:285 (2010)).

Yet other nonlimiting traits include 21-Hydroxylase Deficiency, ABCC8-Related Hyperinsulinism, ARSACS, Achondroplasia, Achromatopsia, Adenosine Monophosphate Deaminase 1, Agenesis of Corpus Callosum with Neuronopathy, Alkaptonuria, Alpha-1-Antitrypsin Deficiency, Alpha-Mannosidosis, Alpha-S arcoglycanopathy, Alpha-Thalassemia, Alzheimers, Angiotensin II Receptor, Type I, Apolipoprotein E Genotyping, Argininosuccinicaciduria, Aspartylglycosaminuria, Ataxia with Vitamin E Deficiency, AtaxiaTelangiectasia, Autoimmune Polyendocrinopathy Syndrome Type 1, BRCA1 Hereditary Breast/Ovarian Cancer, BRCA2 Hereditary Breast/Ovarian Cancer, Bardet-Biedl Syndrome, Best Vitelliform Macular Dystrophy, Beta-Sarcoglycanopathy, Beta-Thalassemia, Biotinidase Deficiency, Blau Syndrome, Bloom Syndrome, CFTR-Related Disorders, CLN3-Related Neuronal Ceroid-Lipofuscinosis, CLN5-Related Neuronal Ceroid-Lipofuscinosis, CLN8-Related Neuronal Ceroid-Lipofuscinosis, Canavan Disease, Carnitine Palmitoyltransferase IA Deficiency, Carnitine Palmitoyltransferase II Deficiency, Cartilage-Hair Hypoplasia, Cerebral Cavernous Malformation, Choroideremia, Cohen Syndrome, Congenital Cataracts, Facial Dysmorphism, and Neuropathy, Congenital Disorder of Glycosylationla, Congenital Disorder of Glycosylation 1b, Congenital Finnish Nephrosis, Crohn Disease, Cystinosis, DFNA 9 (COCH), Diabetes and Hearing Loss, Early-Onset Primary Dystonia (DYTI), Epidermolysis Bullosa Junctional, Herlitz-Pearson Type, FANCC-Related Fanconi Anemia, FGFR1-Related Craniosynostosis, FGFR2-Related Craniosynostosis, FGFR3-Related Craniosynostosis, Factor V Leiden Thrombophilia, Factor V R2 Mutation Thrombophilia, Factor XI Deficiency, Factor XIII Deficiency, Familial Adenomatous Polyposis, Familial Dysautonomia, Familial Hypercholesterolemia Type B, Familial Mediterranean Fever, Free Sialic Acid Storage Disorders, Frontotemporal Dementia with Parkinsonism-17, Fumarase deficiency, GJB2-Related DFNA 3 Nonsyndromic Hearing Loss and Deafness, GJB2-Related DFNB 1 Nonsyndromic Hearing Loss and Deafness, GNE-Related Myopathies, Galactosemia, Gaucher Disease, Glucose-6-Phosphate Dehydrogenase Deficiency, Glutaricacidemia Type 1, Glycogen Storage Disease Type 1a, Glycogen Storage Disease Type 1b, Glycogen Storage Disease Type II, Glycogen Storage Disease Type III, Glycogen Storage Disease Type V, Gracile Syndrome, HFE Associated Hereditary Hemochromatosis, Halder AIMs, Hemoglobin S Beta-Thalassemia, Hereditary Fructose Intolerance, Hereditary Pancreatitis, Hereditary Thymine-Uraciluria, Hexosaminidase A Deficiency, Hidrotic Ectodermal Dysplasia 2, Homocystinuria Caused by Cystathionine Beta-Synthase Deficiency, Hyperkalemic Periodic Paralysis Type 1, Hyperornithinemia-Hyperammonemia-Homocitrullinuria Syndrome, Hyperoxaluria, Primary, Type 1, Hyperoxaluria, Primary, Type 2, Hypochondroplasia, Hypokalemic Periodic Paralysis Type 1, Hypokalemic Periodic Paralysis Type 2, Hypophosphatasia, Infantile Myopathy and Lactic Acidosis (Fatal and Non-Fatal Forms), Isovaleric Acidemias, Krabbe Disease, LGMD2I, Leber Hereditary Optic Neuropathy, Leigh Syndrome, French-Canadian Type, Long Chain 3-Hydroxyacyl-CoA Dehydrogenase Deficiency, MELAS, MERRF, MTHFR Deficiency, MTHFR Thermolabile Variant, MTRNRI-Related Hearing Loss and Deafness, MTTSI-Related Hearing Loss and Deafness, MYH-Associated Polyposis, Maple Syrup Urine Disease Type 1A, Maple Syrup Urine Disease Type 1B, McCune-Albright Syndrome, Medium Chain Acyl-Coenzyme A Dehydrogenase Deficiency, Megalencephalic Leukoencephalopathy with Subcortical Cysts, Metachromatic Leukodystrophy, Mitochondrial Cardiomyopathy, Mitochondrial DNA-Associated Leigh Syndrome and NARP, Mucolipidosis IV, Mucopolysaccharidosis Type I, Mucopolysaccharidosis Type IIIA, Mucopolysaccharidosis Type VII, Multiple Endocrine Neoplasia Type 2, Muscle-Eye-Brain Disease, Nemaline Myopathy, Neurological phenotype, Niemann-Pick Disease Due to Sphingomyelinase Deficiency, Niemann-Pick Disease Type Cl, Nijmegen Breakage Syndrome, PPTI-Related Neuronal Ceroid-Lipofuscinosis, PROPI-related pituitary hormome deficiency, Pallister-Hall Syndrome, Paramyotonia Congenita, Pendred Syndrome, Peroxisomal Bifunctional Enzyme Deficiency, Pervasive Developmental Disorders, Phenylalanine Hydroxylase Deficiency, Plasminogen Activator Inhibitor I, Polycystic Kidney Disease, Autosomal Recessive, Prothrombin G20210A Thrombophilia, Pseudovitamin D Deficiency Rickets, Pycnodysostosis, Retinitis Pigmentosa, Autosomal Recessive, Bothnia Type, Rett Syndrome, Rhizomelic Chondrodysplasia Punctata Type 1, Short Chain Acyl-CoA Dehydrogenase Deficiency, Shwachman-Diamond Syndrome, Sjogren-Larsson Syndrome, Smith-Lemli-Opitz Syndrome, Spastic Paraplegia 13, Sulfate Transporter-Related Osteochondrodysplasia, TFR2-Related Hereditary Hemochromatosis, TPP1-Related Neuronal Ceroid-Lipofuscinosis, Thanatophoric Dysplasia, Transthyretin Amyloidosis, Trifunctional Protein Deficiency, Tyrosine Hydroxylase-Deficient DRD, Tyrosinemia Type 1, Wilson Disease, X-Linked Juvenile Retinoschisis, and Zellweger Syndrome Spectrum.

The methods of assessing the probability that progeny will express certain traits, as described herein, can be implemented into systems, programs, and/or services, which can be authorized by, referred by, and/or performed by, e.g., agencies, public or private companies, genetic counseling centers, dating or match-making services, sperm banks, egg providers, reproductive service providers, fertility clinics, or specialty laboratories Virtual Progeny Assessment and Genetic Counseling Referral System In one example, the methods described herein are integrated into a testing service that can provide information to a couple on the probability that the couple's offspring will express one or more traits described herein, such as risk of a disease. In addition to the results of the Virtual Progeny assessment, referrals to genetic counselors and/or other relevant medical professionals can be provided in order to provide for follow up testing and consultation.

In certain embodiments, a Virtual Progeny assessment begins with a customer order, and the customer can pay a service provider a fee in exchange for the assessment. A customer can be a two potential parents, e.g., partners. Alternatively, a customer can be a physician, a genetic counselor, a medical center, an insurance company, a website, a dating service, a matchmaking service, a pharmaceutical company, or a laboratory testing service provider, who places an order on behalf of two potential parents. For example, a customer can be two prospective parents who seek to learn whether their offspring will be at risk for developing disease. After a customer places an order, DNA collection kits can be sent to the prospective parents, who can deposit a biological sample described herein into the collection kits. The collection kits can then be returned to the company for sending to a specialty lab or can be returned directly to the specialty lab for performing the assessment. A specialty lab, either internal within the company, contracted to work with the company, or external from the company, can isolate the potential parents' DNA from the provided samples for genome scanning from which Virtual Progeny can be generated, as described herein. After analysis of the Virtual Progeny, the results can be provided to the potential parents. The results can inform the potential parents of the chances that their future offspring will express one or more traits, such as traits described herein. In certain instances, the potential parents can also receive, for example, direct phone consultation with a genetic counselor employed by the company, or contact information for genetic counselors and/or other medical professionals who can provide the potential parents with follow up testing and consultation.

Virtual Progeny Assessment and Dating/Marriage Services

In other instances, the methods described herein can be used to allow for the evaluation of potential partners in connection with a matchmaking service. In one example, a Virtual Progeny assessment can be offered to a customer in connection with a matchmaking service, for example, through a single company or a co-marketing or partnership relationship. A user of a matchmaking service can order an assessment of Virtual Progeny described herein to determine the probability that an offspring resulting from the potential match between the user and a candidate partner will express one or more traits described herein. The user can then use this information to aid in evaluating the candidate partner for a potential match. The matchmaking service can be an on-line service, such as Shaadi.com, eHarmony.com and Match.com.

In a particular application, assessment of Virtual Progeny begins with a customer order, where the customer pays a fee in exchange for the assessment. For example, a customer can be a user of a matchmaking service who is interested in evaluating another user for a suitable match. Such a customer can use an assessment of Virtual Progeny described herein to learn whether the potential offspring of a match between such customer and a candidate partner will express one or more traits, such as risk of disease. After selecting a candidate partner to evaluate, a customer can pay for both the customer's and the candidate partner's initial genomic scans with the candidate partner's consent. In other instances, the customer and the candidate partner can also pay separately for the initial genomic scans. After a customer places an order, DNA collection kits can be sent to the customer and the candidate partner, and the customer and the candidate partner can each deposit a biological sample into the collection kit. The collection kits can then be returned to the company for sending to a specialty lab or can be returned directly to the specialty lab for processing according to the methods described herein. A specialty lab, either internal within the company, contracted to work with the company, or external from the company, can perform genomic scans on the customer's and candidate partner's DNA from the provided sample and perform an assessment of Virtual Progeny using the methods described herein. The results of the assessment can then be provided to the customer and/or the candidate partner, and the customer and/or the candidate partner can use the results of the assessment in determining whether the other party is a suitable match.

Virtual Progeny Assessment and Sperm Donors/Egg Donors

In other applications, a female client seeking to have a child can have a Virtual Progeny assessment performed with one or more sperm donors to aid in selecting a donor. In one exemplary method, potential sperm donors are first recruited by a sperm bank Donors who complete the screening process and are considered qualified by the sperm bank then provide a biological sample (such as a buccal swab) that can be processed to obtain whole DNA sequence, SNP genotypes, CNV genotypes or any other digital genetic information.

A female client also provides a biological sample, such as a buccal swab, which is used to generate a genome profile for the female client. The female client genome is then recombined computationally with each donor genome to generate a series of independent Virtual Progeny genomes, as described herein, representing each potential donor-client combination. Each Virtual Progeny genome can then be assessed for the probability of exhibiting one or more traits, such as increased risk of disease. In certain instances, incompatible donor-client combinations are subtracted from the total donor pool to obtain a client-specific filtered donor pool, which can be used, e.g., as a starting point for further selection by the client. In other instances, a client can be given information on the probability of the incidence of one or more traits from donor-client combinations, such as traits preselected by the client, for further sperm donor selection by the client.

In other applications, a male client seeking to have a child can have a Virtual Progeny assessment performed with one or more egg donors to aid in selecting a donor. Egg donors can provide a biological sample (such as a buccal swab) to generate a genome profile for the egg donor, as described herein. The male client also provides a biological sample, such as a buccal swab, which is used to generate a genome profile for the male client. The male client genome is then recombined computationally with each egg donor genome to generate a series of independent Virtual Progeny genomes, as described herein, representing each potential donor client combination. Each Virtual Progeny genome can then be assessed for the probability of exhibiting one or more traits, such as increased risk of disease. In certain instances, incompatible donor-client combinations are subtracted from the total donor pool to obtain a client-specific filtered donor pool, which can be used, e.g., as a starting point for further selection by the client. In other instances, a client can be given information on the probability of the incidence of one or more traits from donor-client combinations, such as traits preselected by the client, for further egg donor selection by the client.

In yet other applications, a heterosexual couple seeking to use a sperm or egg donor to have a child can use Virtual Progeny assessments to screen potential donors. For example, the couple may seek a sperm donor, and the female partner will be the genetic parent of offspring with the sperm donor. Alternatively, the couple may seek an egg donor, and the male partner will be the genetic parent of offspring with the egg donor. In such instances, two rounds of Virtual Progeny assessments can be performed. A first round of Virtual Progeny assessment is performed using biological samples from the heterosexual couple. A second round of Virtual Progeny assessment is performed between the genetic parent and one or more potential donors. The results of the first round of Virtual Progeny assessment can then be compared with the results of the second round, and a donor can be chosen whose Virtual Progeny exhibits an acceptable amount of matching in one or more traits with the Virtual Progeny from the heterosexual couple.

In still other applications, a female homosexual couple seeking to use a sperm donor to have a child can use Virtual Progeny assessments to screen potential sperm donors. Only one of the female partners will be the genetic parent of offspring with the sperm donor. A first round of Virtual Progeny assessment is performed using biological samples from the homosexual couple. A second round of Virtual Progeny assessment is performed between the genetic female parent and one or more potential sperm donors. The results of the first round of Virtual Progeny assessment can then be compared with the results of the second round, and a sperm donor can be chosen whose Virtual Progeny exhibits an acceptable amount of matching in one or more traits with the Virtual Progeny from the homosexual couple. In some situations, a Virtual Progeny assessment is also performed with the second female partner and one or more potential sperm donors, and a donor is selected whose Virtual Progeny exhibits an acceptable amount of matching in one or more traits with the Virtual Progeny from the homosexual couple.

In yet other applications, a male homosexual couple seeking to use an egg donor to have a child can use Virtual Progeny assessments to screen potential egg donors. Only one of the male partners will be the genetic parent of offspring with the egg donor. A first round of Virtual Progeny assessment is performed using biological samples from the homosexual couple. A second round of Virtual Progeny assessment is performed between the genetic male parent and one or more potential egg donors. The results of the first round of Virtual Progeny assessment can then be compared with the results of the second round, and an egg donor can be chosen whose Virtual Progeny exhibits an acceptable amount of matching in one or more traits with the Virtual Progeny from the homosexual couple. In some situations, a Virtual Progeny assessment is also performed with the second male partner and one or more potential egg donors, and a donor is selected whose Virtual Progeny exhibits an acceptable amount of matching in one or more traits with the Virtual Progeny from the homosexual couple.

In further applications of the methods disclosed herein, the risk of disease in a potential progeny can be assessed, as well as the likelihood of expressing a genetically influenced trait. As with the other methods disclosed, a DNA sample from a first genomic DNA are obtained from a first potential parent and a second genomic DNA sample from a second potential parent. The presence or absence of one or more nucleotide variants are identified at one or more loci of at least one pair of chromosomes of the first and the second genomic DNA samples and these identified nucleotide variants for the first and second genomic DNA samples are compared to a plurality of predetermined genomic sequences of haplotypes having predetermined frequencies at predetermined loci to identify haplotypes present in the first and second genomic DNA samples. A first diploid genome profile for the first potential parent is constructed. The first genome profile comprises the identified haplotypes in the first genomic DNA sample and a linkage probability determined by the frequencies of the identified haplotypes in the plurality of predetermined genomic sequences. A second diploid genome profile for the second potential parent is constructed. The second genome profile comprises the identified haplotypes in the second genomic DNA sample and a linkage probability determined by the frequencies of the identified haplotypes in the plurality of predetermined genomic sequences. A first library is constructed that comprises potential haploid gamete genomes from the first diploid genome profile by generating a combination of the haplotypes identified in the first genomic DNA sample using the linkage probability for each combination of the identified haplotypes, while a second library is constructed that comprises potential haploid gamete genomes from the second diploid genome profile by generating a combination of the haplotypes identified in the second genomic DNA sample using the linkage probability for each combination of the identified haplotypes. The method also entails combining a first haploid gamete genome from the first library with a second haploid gamete genome from the second library to form a diploid progeny genome. The diploid progeny genome is compared to a database of genomes relating to disease-associated or genetically influenced traits, thereby assessing the risk of disease or the likelihood of expressing a genetically influenced trait of the potential progeny.

Computer Systems/Processors

The methods and systems described herein can be used in combination with one or more processors, having either single or multiple cores. The processor can be operatively connected to a memory. For instance, the memory can be solid state, flash, or nanoparticle based. The processor and/or memory can be operatively connected to a network via a network adapter. The network can be digital, analog, or a combination of the two. The processor can be operatively connected to the memory to execute computer program instructions to perform one or more steps described herein. Any computer language known to those skilled in the art can be used.

Input/output circuitry can be included to provide the capability to input data to, or output data from, the processor and/or memory. For example, input/output circuitry can include input devices, such as keyboards, mice, touch pads, trackballs, scanners, and the like, output devices, such as video adapters, monitors, printers, and the like, and input/output devices, such as, modems and the like.

The memory can store program instructions that are executed by, and data that are used and processed by, CPUs to perform various functions. The memory can include electronic memory devices, such as random-access memory (RAM), read-only memory (ROM), programmable read-only memory (PROM), electrically erasable programmable read-only memory (EEPROM), and flash memory, and electro-mechanical memory, such as magnetic disk drives, tape drives, and optical disk drives, which can be used as an integrated drive electronics (IDE) interface, or a variation or enhancement thereof, such as enhanced IDE (EIDE) or ultra direct memory access (UDMA), or a small computer system interface (SCSI) based interface, or a variation or enhancement thereof, such as fast-SCSI, wide-SCSI, fast and wide-SCSI, etc, or a fiber channel-arbitrated loop (FC-AL) interface.

The systems described herein can also include an operating system that runs on the processor, including UNIX®, OS/2®, and Windows®, each of which can be configured to run many tasks at the same time, e.g., a multitasking operating systems. In one aspect, the methods are utilized with a wireless communication and/or computation device, such as a mobile phone, personal digital assistant, personal computer, and the like. Moreover, the computing system can be operable to wirelessly transmit data to wireless or wired communication devices using a data network, such as the Internet, or a local area network (LAN), wide-area network (WAN), cellular network, or other wireless networks known to those skilled in the art.

In one embodiment, a graphical user interface can be included to allow human interaction with the computing system. The graphical user interface can comprise a screen, such as an organic light emitting diode screen, liquid crystal display screen, thin film transistor display, and the like. The graphical user interface can generate a wide range of colors, or a black and white screen can be used.

In certain instances, the graphical user interface can be touch sensitive, and it can use any technology known to skilled artisans including, but not limited to, resistive, surface acoustic wave, capacitive, infrared, strain gauge, optical imaging, dispersive signal technology, acoustic pulse recognition, frustrated total internal reflection, and diffused laser imaging.

The methods and compositions disclosed herein are further illustrated by the following examples. The examples are provided for illustrative purposes only. They are not to be construed as limiting the scope or content of the invention in any way.

Example 1

Generation of Virtual Progeny Genome

In this particular example, the generation of a Virtual Progeny genome is a four step process. One of ordinary skill in the art will understand that other steps may be added, combined, or deleted as desired.

Step 1—Genome Scans

Processing is accomplished with the use of DNA microarrays, DNA sequencing protocols, or other DNA reading technologies. In the present example, a DNA microarray is used to generate information relating to loci of interest. This information is utilized to produce genome scans that include genotype information from the plurality of loci of interest, which are defined by single base polymorphisms ("SNPs or CNPs"), DNA sequence reads, copy number, or other forms of personal genetic information. In the present example, Jane Doe and John Smith provided samples, which have such information provided for loci 01 through N (FIG. 1A).

Step 2—Expansion of Genome Scans to Generate Genome Profiles

Existing population datasets, genome scans of family members, and a variety of computational tools and algorithms, known to those skilled in the art, may be used in combination with each person's genome scan to distinguish haplotypes, impute genotypes at additional loci, and establish long-range genetic phasing. The derived genome profile preferably incorporates phasing information in the form of stochastic matrices between haplotypes. An example of haplotype structure is shown in the figure below: loci 01-04 are inherited as an indivisible block, which is a haplotype. Stochastic matrices between loci 05 and 06 are shown in block boxes for John and Jane (FIG. 1B).

Figure 1C:
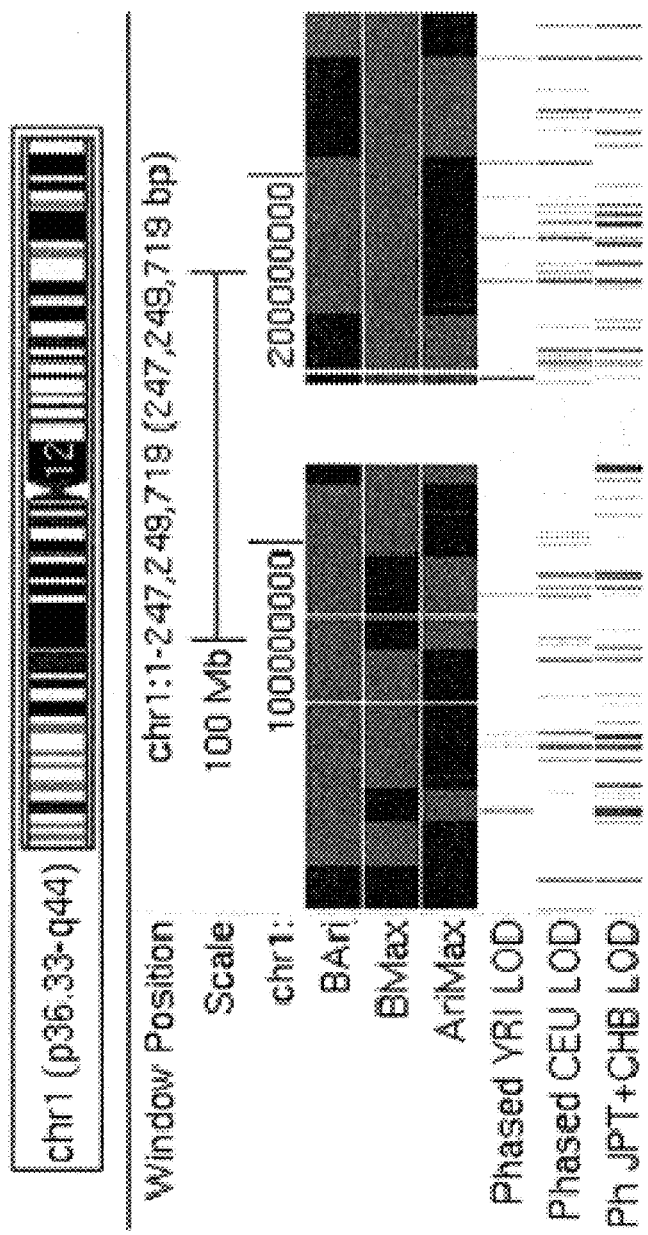
FIG. 1C is a schematic illustration showing the genome profile for John Smith, taking into account the profile for loci 01 through N.

With genome scans performed on two or more related persons, phasing information is extended. In an example of genome analysis, the UCSC genome browser is used to display phasing over large maternally-inherited chromosomal segments that comprise 100 million base pairs or more (FIG. 1C). A Monte Carlo simulation or Markov process as described above is used to generate haplopaths through a genome, where haplotypes are transmitted intact, and stochastic matrices are used to move from one haplotype or locus to the next one. In the example, John Smith's genome is converted into a series of haplopaths by means of a Monte Carlo simulation (FIG. 1D).

Figure 1E:
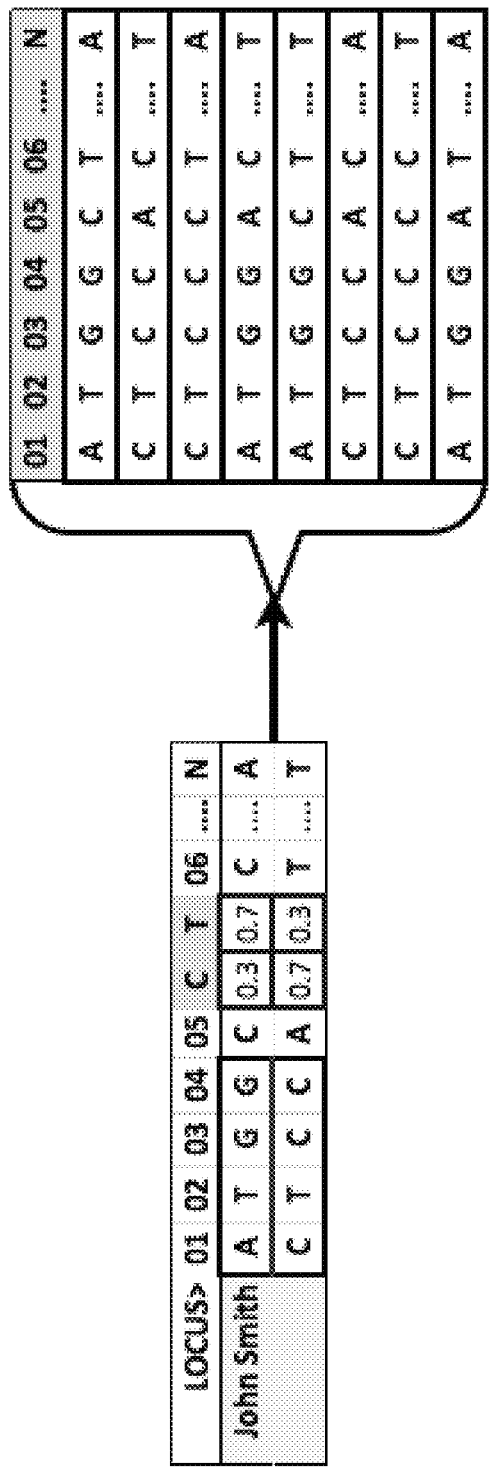
FIG. 1E is a schematic illustration showing the haplopaths in rows 1 and 7 for John Smith.

Each individual genome profile is used to generate a pool of VirtualGametes (FIG. 1E). Exemplary haplopaths in rows 1 and 7 are illustrated.

Step 4—Virtual Progeny Permutations from Random Virtual Gametes from Each Individual Single Virtual Gametes from each person is chosen randomly and combined to produce one permutation of a Virtual Progeny genome. The process of Virtual Gamete choice and reproductive combination to produce a diploid genome is iterated a sufficient number of times such that the normalized sum of Virtual Progeny permutations provides a stable estimate of the Virtual Progeny genome probability distribution. For instance, the number of iterations may be between about 10 and about 100. More preferably, the number of iterations may be between about 100 and about 1000. Most preferably, the number of iterations may be between about 1000 and about 100,000. In another aspect, the number of iterations may be about 50 or greater. More preferably, the number of iterations may be about 150 or greater. Most preferably, the number of iterations may be about 3000 or greater.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of genetic screening for a first potential parent and a second potential parent, the method implemented by one or more computer processors executing program instructions, the method comprising:
   (a) using the processors, obtaining a first genome profile containing first genotypes in a sequence of genetic loci, the first genome profile generated by a first DNA sequencer scanning a biological sample from the first potential parent;
   (b) using the processors, obtaining a second genome profile containing second genotypes in the sequence of genetic loci, the second genome profile generated by a second DNA sequencer scanning a biological sample from the second potential parent;
   (c) using the processors, generating a first haplopath from the first genome profile of the first potential parent using a Monte Carlo simulation, wherein the first haplopath represents a first sequence of haploid alleles corresponding to the sequence of genetic loci, the first haplopath including at least 10,000 base pairs;
   (d) using the processors, selecting each allele in the first sequence of haploid alleles, wherein said selecting comprises:
      (i) retrieving a first linkage probability that is determined based on linkage disequilibrium within a first population to which the first potential parent belong, and
      (ii) selecting a particular allele for the first sequence of haploid alleles at a particular locus based on a preceding allele selected for a preceding locus along the sequence of genetic loci and the first linkage probability between the preceding allele and the particular allele;
   (e) using the processors, generating a second haplopath from the second genome profile of the second potential parent using the Monte Carlo simulation, wherein the second haplopath represents a second sequence of haploid alleles correspond to the sequence of genetic loci, the second haplopath including at least 10,000 base pairs;
   (f) using the processors, selecting each allele in the second sequence of haploid alleles, wherein said selecting comprises:
      (i) retrieving a second linkage probability that is determined based on linkage disequilibrium within a second population to which the second potential parent belong; and
      (ii) selecting a particular allele for the second sequence of haploid alleles at a particular locus based on a preceding allele selected for a preceding locus along the sequence of genetic loci and the second linkage probability between the preceding allele and the particular allele;
   (g) using the processors, forming a diploid genotype profile by matching the first sequence of haploid alleles and the second sequence of haploid alleles in accordance with the sequence of genetic loci, the diploid genotype profile corresponding to the sequence of genetic loci and having a diploid genotype at each locus of the sequence of genetic loci, each diploid genotype at each locus having a first haploid allele from the first sequence of haploid alleles and a second haploid allele from the second sequence of haploid alleles;
(h) using the processors, comparing one of more of the diploid genotypes of the diploid genotype profile to one or more databases of genotype-phenotype associations to determine a likelihood of expression of a set of phenotypes for the potential progeny having the diploid genotype profile;
(i) repeating steps (c)-(h) to generate a plurality of diploid genotype profiles and associated likelihoods of expressing the set of phenotypes; and
(j) based on results of repeating steps (c)-(h), generating probabilities or probability distributions of progenies of the first and second potential parents associating with expressing the set of phenotypes.

2. The method of claim 1, wherein:
the first genome profile of the first potential parent includes phased DNA sequences and the second genome profile includes phased DNA sequences;
generating the first haplopath includes simulating recombination between the phased DNA sequences from the first genome profile; and
generating the second haplopath includes simulating recombination between the phased DNA sequences from the second genome profile.

3. The method of claim 1, wherein, prior to step (a):
variants are identified comprising single base substitutions, insertion/deletions, copy number polymorphisms and combinations thereof at the sequence of genetic loci from DNA samples obtained from the first and second potential parents.

4. The method of claim 3, further comprising:
for each potential parent, using the processors, comparing the identified variants to a plurality of predetermined genomic sequences of haplotypes to identify haplotypes present in the DNA samples obtained from the potential parent; and
using the processors, constructing the first and second genome profiles, wherein each of the genome profiles comprises the identified haplotypes present and association frequencies of consecutive haplotypes, respectively.

5. The method of claim 1, wherein one of the potential parents is selected from the group consisting of a sperm donor, an oocyte donor, and a potential partner.

6. The method of claim 1, wherein each of the diploid genotype profiles represent an iteration of the Monte Carlo simulation.

7. The method of claim 1, wherein the first and second potential parents are opposite-sex partners.

8. The method of claim 1, comprising repeating steps (c)-(j) a sufficient number of times to generate a stable estimate of the probabilities or probability distributions of progenies of the first and second potential parents associating with expressing the set of phenotypes.

9. The method of claim 1, wherein the first and second linkage probabilities are empirically-determined.

10. The method of claim 1, wherein the selection of the particular allele for the first sequence of haploid alleles at the particular locus is further based on one or more rules selected from the group consisting of: recombination suppression, allele segregation, independent assortment, Hardy-Weinberg equilibria, and other probabilistic genetic processes.

11. A non-transitory computer readable medium for storing computer code comprising instructions for performing genetic screening for a first potential parent and a second potential parent, the instructions, when executed by one or more computer processors, cause the one or more computer processors to perform steps comprising:
(a) obtaining a first genome profile containing first genotypes in a sequence of genetic loci, the first genome profile generated by a first DNA sequencer scanning a biological sample from the first potential parent;
(b) obtaining a second genome profile containing second genotypes in the sequence of genetic loci, the second genome profile generated by a second DNA sequencer scanning a biological sample from the second potential parent;
(c) generating a first haplopath from the first genome profile of the first potential parent using a Monte Carlo simulation, wherein the first haplopath represents a first sequence of haploid alleles corresponding to the sequence of genetic loci, the first haplopath including at least 10,000 base pairs;
(d) selecting each allele in the first sequence of haploid alleles, wherein said selecting comprises:
(i) retrieving a first linkage probability that is determined based on linkage disequilibrium within a first population to which the first potential parent belong, and
(ii) selecting a particular allele for the first sequence of haploid alleles at a particular locus based on a preceding allele selected for a preceding locus along the sequence of genetic loci and the first linkage probability between the preceding allele and the particular allele;
(e) generating a second haplopath from the second genome profile of the second potential parent using the Monte Carlo simulation, wherein the second haplopath represents a second sequence of haploid alleles correspond to the sequence of genetic loci, the second haplopath including at least 10,000 base pairs;
(f) selecting each allele in the second sequence of haploid alleles, wherein said selecting comprises:
(i) retrieving a second linkage probability that is determined based on linkage disequilibrium within a second population to which the second potential parent belong; and
(ii) selecting a particular allele for the second sequence of haploid alleles at a particular locus based on a preceding allele selected for a preceding locus along the sequence of genetic loci and the second linkage probability between the preceding allele and the particular allele;
(g) forming a diploid genotype profile by matching the first sequence of haploid alleles and the second sequence of haploid alleles in accordance with the sequence of genetic loci, the diploid genotype profile corresponding to the sequence of genetic loci and having a diploid genotype at each locus of the sequence of genetic loci, each diploid genotype at each locus having a first haploid allele from the first sequence of haploid alleles and a second haploid allele from the second sequence of haploid alleles;
(h) comparing one of more of the diploid genotypes of the diploid genotype profile to one or more databases of genotype-phenotype associations to determine a likelihood of expression of a set of phenotypes for the potential progeny having the diploid genotype profile;

(i) repeating steps (c)-(h) to generate a plurality of diploid genotype profiles and associated likelihoods of expressing the set of phenotypes; and (j) based on results of repeating steps (c)-(h), generating probabilities or probability distributions of progenies of the first and second potential parents associating with expressing the set of phenotypes.

12. The non-transitory computer readable medium of claim 11, wherein:
the first genome profile of the first potential parent includes phased DNA sequences and the second genome profile includes phased DNA sequences;
generating the first haplopath includes simulating recombination between the phased DNA sequences from the first genome profile; and
generating the second haplopath includes simulating recombination between the phased DNA sequences from the second genome profile.

13. The non-transitory computer readable medium of claim 11, wherein, prior to step (a):
variants are identified comprising single base substitutions, insertion/deletions, copy number polymorphisms and combinations thereof at the sequence of genetic loci from DNA samples obtained from the first and second potential parents.

14. The non-transitory computer readable medium of claim 13 wherein the steps further comprises:
for each potential parent, using the processors, comparing the identified variants to a plurality of predetermined genomic sequences of haplotypes to identify haplotypes present in the DNA samples obtained from the potential parent; and
using the processors, constructing the first and second genome profiles, wherein each of the genome profiles comprises the identified haplotypes present and association frequencies of consecutive haplotypes, respectively.

15. The non-transitory computer readable medium of claim 11, wherein each of the diploid genotype profiles represent an iteration of the Monte Carlo simulation.

16. The non-transitory computer readable medium of claim 11, wherein the first and second potential parents are opposite-sex partners.

17. The non-transitory computer readable medium of claim 11, wherein the steps further comprise repeating steps (c)-(j) a sufficient number of times to generate a stable estimate of the probabilities or probability distributions of progenies of the first and second potential parents associating with expressing the set of phenotypes.

18. The non-transitory computer readable medium of claim 11, wherein the first and second linkage probabilities are empirically-determined.

19. The non-transitory computer readable medium of claim 11, wherein the selection of the particular allele for the first sequence of haploid alleles at the particular locus is further based on one or more rules selected from the group consisting of:
recombination suppression, allele segregation, independent assortment, Hardy-Weinberg equilibria, and other probabilistic genetic processes.

20. A system comprising:
one or more computer processors; and
memory for storing computer code comprising instructions for performing genetic screening for a first potential parent and a second potential parent, the instructions, when executed by one or more computer processors, cause the one or more computer processors to perform steps comprising:

(a) obtaining a first genome profile containing first genotypes in a sequence of genetic loci, the first genome profile generated by a first DNA sequencer scanning a biological sample from the first potential parent;

(b) obtaining a second genome profile containing second genotypes in the sequence of genetic loci, the second genome profile generated by a second DNA sequencer scanning a biological sample from the second potential parent;

(c) generating a first haplopath from the first genome profile of the first potential parent using a Monte Carlo simulation, wherein the first haplopath represents a first sequence of haploid alleles corresponding to the sequence of genetic loci, the first haplopath including at least 10,000 base pairs;

(d) selecting each allele in the first sequence of haploid alleles, wherein said selecting comprises:
(i) retrieving a first linkage probability that is determined based on linkage disequilibrium within a first population to which the first potential parent belong, and
(ii) selecting a particular allele for the first sequence of haploid alleles at a particular locus based on a preceding allele selected for a preceding locus along the sequence of genetic loci and the first linkage probability between the preceding allele and the particular allele;

(e) generating a second haplopath from the second genome profile of the second potential parent using the Monte Carlo simulation, wherein the second haplopath represents a second sequence of haploid alleles correspond to the sequence of genetic loci, the second haplopath including at least 10,000 base pairs;

(f) selecting each allele in the second sequence of haploid alleles, wherein said selecting comprises:
(i) retrieving a second linkage probability that is determined based on linkage disequilibrium within a second population to which the second potential parent belong; and
(ii) selecting a particular allele for the second sequence of haploid alleles at a particular locus based on a preceding allele selected for a preceding locus along the sequence of genetic loci and the second linkage probability between the preceding allele and the particular allele;

(g) forming a diploid genotype profile by matching the first sequence of haploid alleles and the second sequence of haploid alleles in accordance with the sequence of genetic loci, the diploid genotype profile corresponding to the sequence of genetic loci and having a diploid genotype at each locus of the sequence of genetic loci, each diploid genotype at each locus having a first haploid allele from the first sequence of haploid alleles and a second haploid allele from the second sequence of haploid alleles;

(h) comparing one of more of the diploid genotypes of the diploid genotype profile to one or more databases of genotype-phenotype associations to determine a likelihood of expression of a set of phenotypes for the potential progeny having the diploid genotype profile;

(i) repeating steps (c)-(h) to generate a plurality of diploid genotype profiles and associated likelihoods of expressing the set of phenotypes; and
(j) based on results of repeating steps (c)-(h), generating probabilities or probability distributions of progenies of the first and second potential parents associating with expressing the set of phenotypes.

* * * * *